United States Patent [19]

Esser et al.

[11] Patent Number: 5,596,000
[45] Date of Patent: Jan. 21, 1997

[54] AMINO ACID DERIVATIVES, PROCESSES FOR THE MANUFACTURE THEREOF AND PHARMACEUTICAL COMPOSITIONS CONTAINING THESE COMPOUNDS

[75] Inventors: Franz Esser; Gerd Schnorrenberg; Horst Dollinger, all of Ingelheim am Rhein; Birgit Jung; Erich Burger, both of Bingen/Rhein, all of Germany

[73] Assignee: Boehringer Ingelheim KG, Ingelheim am Rhein, Germany

[21] Appl. No.: 116,090

[22] Filed: Sep. 2, 1993

[30] Foreign Application Priority Data

Sep. 3, 1992 [DE] Germany .......................... 42 29 447.9
Dec. 22, 1992 [DE] Germany .......................... 42 43 496.3
May 8, 1993 [DE] Germany .......................... 43 15 437.9

[51] Int. Cl.$^6$ .................. A61K 31/47; A61K 31/415
[52] U.S. Cl. .................. 514/312; 514/221; 514/290; 514/253; 514/414; 514/218; 540/523; 540/575; 540/553; 544/373; 544/372; 546/101; 546/158; 548/468; 548/482; 548/493
[58] Field of Search ............................... 514/312

[56] References Cited

U.S. PATENT DOCUMENTS 5,104,884  4/1992  Korodi et al. .......................... 514/312

Primary Examiner—Robert T. Bond
Attorney, Agent, or Firm—R. P. Raymond; M-E. M. Devlin; A. R. Stempel

[57] ABSTRACT

The invention relates to new amino acid derivatives of general formula I

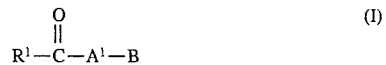

and the pharmaceutically acceptable salts thereof, wherein group B is $-A^2-NR^2R^3$ or $R^5$, wherein group $R^5$ is

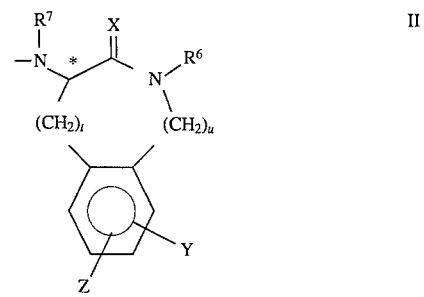

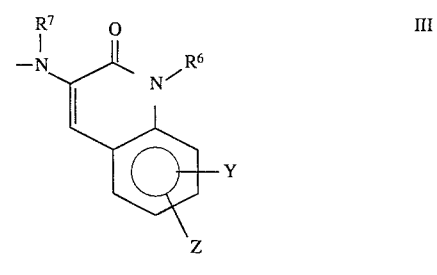

or

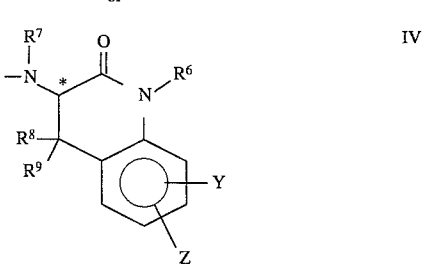

and $R^1$, $A^1$, $A^2$, $R^2$, $R^3$, $R^6$, $R^7$, $R^8$, $R^9$, X, Y, Z, t and u have the meanings described in the specification, as well as the preparation and use thereof. The novel compounds are valuable neurokinin (tachykinin) antagonists.

16 Claims, No Drawings

AMINO ACID DERIVATIVES, PROCESSES FOR THE MANUFACTURE THEREOF AND PHARMACEUTICAL COMPOSITIONS CONTAINING THESE COMPOUNDS

The invention relates to new amino acid derivatives of general formula I,

wherein B represents the group $-A^2-NR^2R^3$ or $R^5$, and the pharmaceutically acceptable salts thereof, processes for their preparation and pharmaceutical compositions containing these compounds. The compounds are valuable neurokinin (tachykinin)-antagonists.

European Patent Applications EP 394 989 and EP 443 132 disclose peptides with a neurokinin-antagonistic action. The compounds according to the invention differ significantly from these peptides in the members $A^2$, $R^5$ and

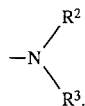

The abbreviations used for the amino acids in this specification and the claims correspond to the conventional three letter code described for example in Europ. J. Biochem., 138, 9 (1984). The other abbreviations are explained as follows:

| | |
|---|---|
| Boc = | t-Butoxycarbonyl |
| Bzl = | Benzyl |
| CDI = | Carbonyldiimidazole |
| Cha = | 3-Cyclohexylalanine |
| DCCI = | Dicyclohexylcarbodiimide |
| DCH = | Dicyclohexylurea |
| HOBt = | 1-Hydroxybenzotriazole |
| Hpa = | Homophenylalanine |
| Hyp = | (2S,4R)-Hydroxyproline |
| Pal = | 3-(1-Pyrrolyl)alanine |
| THF = | Tetrahydrofuran |
| TFA = | Trifluoroacetic acid |
| Z = | Benzyloxycarbonyl |
| Me = | Methyl |
| Ac = | Acetyl |
| Et = | Ethyl |
| DMF = | Dimethylformamide |
| DPPA = | Diphenylphosphorylazide |
| PPA = | Polyphosphoric acid |
| RT = | ambient temperature |

Unless explicitly indicated otherwise in the following text, the expression amino acid covers natural and unnatural amino acids, both of the D- and L-form, more particularly α-amino acids as well as the isomers thereof.

If an amino acid is given without prefix (e.g. Orn) this indicates the L-form of the amino acids. The D-form is explicitly indicated.

The invention relates to new amino acid derivatives of general formula I

and the pharmaceutically acceptable salts thereof, wherein $R^1$ is vinyl, aryl, heteroaryl, aralkyl, heteroaralkyl, arylvinyl, heteroarylvinyl, aryloxyalkyl, arylalkyloxy, $(C_{3-8})$ cycloalkyl, $(C_{3-8})$cycloalkylalkyl, bicycloheptyl or bicycloheptylalkyl (either unsubstituted or substituted by 1–3 methyl groups), adamantyl, adamantylalkyl, decalin, decalinalkyl, tetraline, tetralinalkyl, diphenylalkyl, di(arylalkyl)aminoalkyl or arylalkylaminoalkyl (wherein aryl is phenyl, mono-, di- or trisubstituted phenyl or naphthyl; the substituents of the phenyl group represent, independently of each other, halogen, trihalomethyl, alkoxy, alkyl, hydroxy, nitro, alkylcarbonyl or cyano; heteroaryl is indolyl, indolyl substituted in position 1 by alkyl or benzyl, pyridyl, pyrrolyl, imidazolyl or thienyl; and the alkyl or alkoxy group contains 1 to 3 carbon atoms;

$A^1$ is D- or L-alanine (Ala, (D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ3,4)-Pro), D- or L-hydroxyproline (Pro(OH)) such as 3-hydroxyproline (Pro(3OH)) and 4-hydroxyproline (Pro(4OH)), D- or L-azetidin-2-carboxylic acid (Azt), D- or L-thioproline (Tpr), D- or L-aminoproline (Pro(NH$_2$)) such as 3-aminoproline (Pro(3NH$_2$)) and 4-aminoproline (Pro(4NH$_2$)), D- or L-pyroglutamic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Ash), D- or L-lysine (Lys), D- or L-arginine (Arg), D- or L-histidine (His), D- or L-ornithine (Orn), D- or L-hydroxy piperidine carboxylic acid such as 5-hydroxypiperidine-2-carboxylic acid, D- or L-mercaptoproline (Pro(SH)) such as 3-mercaptoproline (Pro(3SH)) and 4-mercaptoproline (Pro)4SH)), Tpr(O), Met(O), Tpr(O$_2$) or Met(O$_2$), and the geometric isomers thereof, whereby the hydroxy and amino groups contained therein may be protected by usual protective groups (e.g. acyl, carbamoyl or aralkyl (in particular benzyl));

B is group $-A^2-NR^2R^3-$ or $-R^5$;

$A^2$ is a lipophile α-amino acid which contains a phenyl, 1-, 2- or 3-substituted phenyl, heteroaryl, cyclohexyl or cyclopentyl group, a naphthyl group or a mono- or di-$C_{1-3}$-alkylamino group, and this cyclic group or amino group is separated by 1- to 8-membered chain from the backbone of the amino acid, (whereby the substituents of the phenyl group may, independently of each other, be halogen, trihalomethyl, alkoxy, alkyl, cyano or 1-pyrrolidinyl and whereby in the 1- to 8-membered chain, the members of the chain may be $-CHR^4$, $-C(O)-$, $-O-$, $-S-$ and/or $-NR^4-$ which are arranged such that they result in one of the following three types of chains $(CHR^4)_{1-8}-$ $(CHR^4)_{0-p}-G^1-(CHR^4)_{0-q}-$ $(CHR^4)_{1-p}-G^2-(CHR^4)_{0-q}-$ wherein $G^1$ is $-C(O)O-$ or $-C(O)-NR^4-$, $G^2$ is $-O-$, $-S-$, $-NR^4-C(O)-O-$, $-NR^4-C(O)-$, $-NR^4-C(O)-NR^4-$ or $-O-C(O)-NR^4-$ and p and q are whole numbers from 1 to 6 which are chosen such that the total number of the chain members is 1 to 8, and $R^4$ is hydrogen, alkyl, aryl or aralkyl, wherein aryl is phenyl, mono-, di- or trisubstituted phenyl or naphthyl; the substituents of the phenyl group are, independently of each other halogen, trihalomethyl, alkoxy, alkyl or cyano, and the alkyl group contains 1 to 3 carbon atoms; (whereby, if one chain contains more than one $-CHR^4$-group, $R^4$ can only be alkyl, aryl or aralkyl in one of these $-CHR^4$-groups and whereby the chain is not $CH_2$, if $R^2$ and $R^3$ are alkyl or aralkyl and if

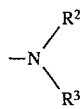

together form the group

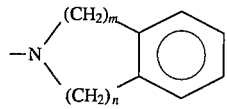

and m and n are each 0, 1, 2 or 3, wherein the sum thereof is 2, 3, 4 or 5) or $A^2$ is Leu, Ile, Nle, Val, Met or one of the groups

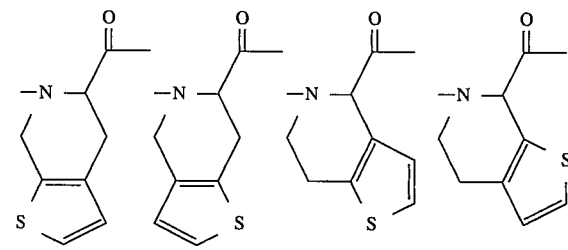

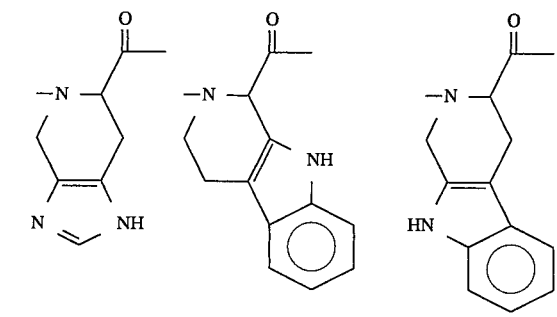

and

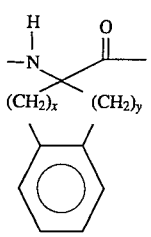

(wherein x and y independently of each other are 1 or 2);

$R^2$ and $R^3$ independently of each other are alkyl, arylalkyl, heteroaryl or hydroxy (wherein aryl is phenyl, mono-, di- or trisubstituted phenyl or naphthyl; the substituents of the phenyl group are, independently of each other halogen, trihalomethyl, alkoxy, alkyl, alkylthio, hydroxy, nitro, trifluoromethoxy, dialkylamino or cyano or 2 adjacent positions of the phenyl group are linked by —O—$(CH_2)_{1\ or\ 2}$—O—; heteroaryl is indolyl, pyridyl, pyrrolyl, imidazolyl or thienyl; and the alkyl or alkoxy group contains 1 to 3 carbon atoms) or the group

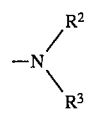

is a ring of general formula

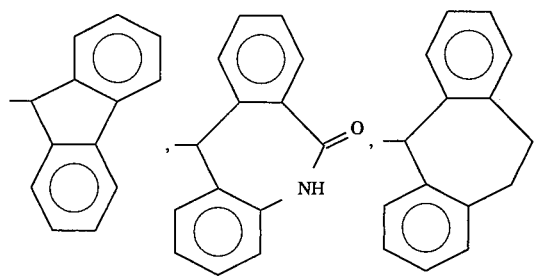

or

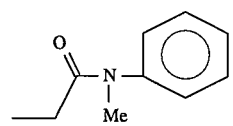

wherein m and n are each 0, 1, 2 or 3, whereby the sum thereof is 2, 3, 4 or 5, s is 2 or 3,
W is the group

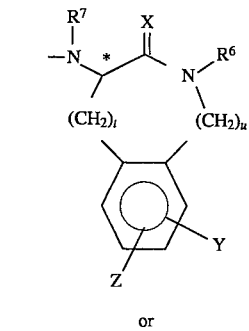

$(CH_2)_{0-2}$-aryl, $CH(aryl)_2$, cyclopentyl, $(CH_2)_{0-2}$-cyclohexyl, pyridyl or (wherein aryl is phenyl, mono-, di- or trisubstituted phenyl or naphthyl; the substituents of the phenyl group independently of each other are halogen, trihalomethyl, alkoxy, alkyl, cyano, hydroxy, nitro or alkylthio or 2 adjacent positions of the phenyl group are linked by —O—$(CH_2)_{1-2}$—O— and alkyl contains 1 to 3 carbon atoms);
$R^5$ is an amine of formula

II or

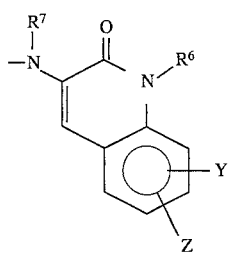

wherein

R⁶ is aralkyl, diarylalkyl (in these groups aryl is phenyl or naphthyl and alkyl ($C_{1-5}$)alkyl), heteroaryl($C_{1-5}$)alkyl (wherein heteroaryl is 2-, 3- or 4-pyridyl or 2- or 3-thienyl), phenylamino-($C_{1-5}$)alkyl, nephthylamino-($C_{1-5}$)alkyl or N-phenylalkylpiperidinyl (wherein the phenyl groups listed are not substituted or contain 1, 2 or 3 substituents which are, independently of each other ($C_{1-5}$)alkyl, preferably methyl, ($C_{1-5}$)alkoxy, preferably methoxy, dimethylamine, halogen, trifluoromethyl, —CN or $OCF_3$);

$R_7$ is hydrogen or ($C_{1-5}$)-alkyl;

X is O or $H_2$;

Y and Z independently of each other are hydrogen, ($C_{1-5}$)alkyl; ($C_{1-5}$)alkyloxy, benzyloxy (wherein the phenyl group is not substituted or contains 1, 2 or 3 substituents which are independently of each other ($C_{1-5}$)alkyl, preferably methyl, ($C_{1-5}$)alkoxy, preferably methoxy, dimethylamine, halogen, trifluoromethyl, —CN or $OCF_3$), $OCF_3$, halogen, $CF_3$, CN, $CH_2NH_2$, $CONH_2$, N-($C_{1-5}$-alkyl)$_2$, NH-($C_{1-4}$)alkylcarbonyl, N-($C_{1-5}$)alkyl-N-($C_{1-4}$)alkylcarbonyl, $NH_2$ or NH-($C_{1-5}$)alkyl or if Y and Z are in a vicinal position to one another, both together represent —$OCH_2O$—, $OCH_2CH_2O$— or $(CH)_4$;

t and u have one of the following meanings (a) t and u are zero (b) t is one and u is zero (c) t and u are each one (d) t is two and u is zero;

and if t is one and u is zero, $R^5$ is also an amine of formula IV

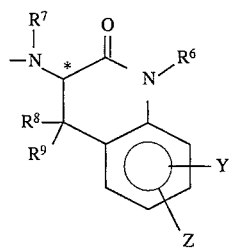

wherein

R⁶, R⁷, Y and Z have the above meanings and

R⁸ is hydrogen and R⁹ is hydroxy, ($C_{1-5}$)alkoxy, phenyl($C_{1-5}$)alkyloxy, naphthyl-($C_{1-5}$)alkyloxy or ($C_{1-4}$)alkylcarbonyl, or wherein R⁸ and R⁹ are both oxygen or —$OCH_2CH_2O$—;

and the chirality to C* may be R or S.

Compounds of general formula I may have acid groups, mainly carboxyl groups or phenolic hydroxy groups, and/or alkaline groups such as guanidino or amino functions. Therefore, compounds of general formula I may be present either as inner salts, as salts with pharmaceutically usable inorganic acids such as hydrochloric acid, sulphuric acid, phosphoric acid, sulphonic acid or organic acids (e.g. maleic acid, fumaric acid, citric acid, tartaric acid or acetic acid) or as salts with pharmaceutically usable bases such as alkali or alkaline earth metal hydroxides or carbonates, zinc or ammonium hydroxides or organic amines such as diethylamine, triethylamine, triethanolamine and the like.

The chiral centres in the new amino acid derivatives may have an R-, S- or R,S-configuration.

The expression "heteroaryl group" contained in the definition of $A^2$ represents a mono-, bi- or tricyclic aromatic ring system which contains 1 or 2 heteroatoms, namely one or two nitrogen atoms or one nitrogen atom and one sulphur atom. The group may optionally contain 1 or 2 substituents ($C_{1-3}$alkyl) or one oxo group or one alkoxy group.

Examples of suitable heteroaryl groups are

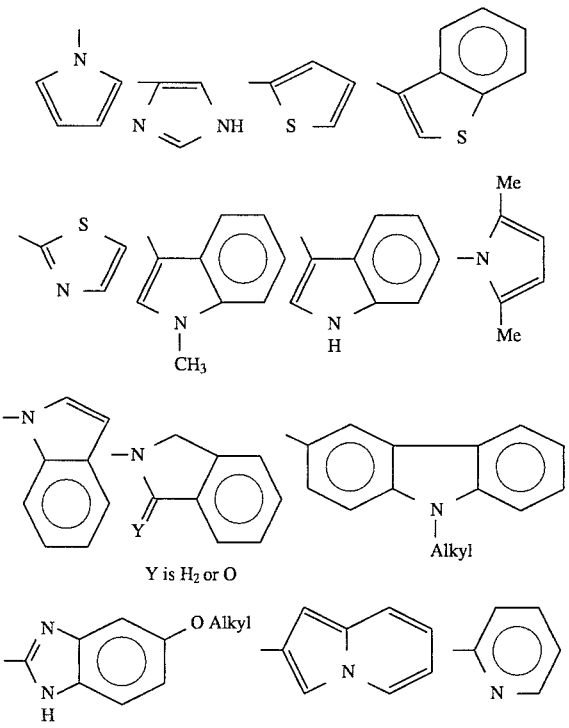

It must be noted that the above heteroaryl groups may also be bound to the chain in positions other than those mentioned.

As mentioned above, the "1- to 8-membered chain" contained in $A^2$ comprises 1 to 8 members denoting the following groups: —$CHR^4$—, —C(O)—, —O—, —S—, —$NR^4$—. The chain is bound to the α-carbon atom of the amino acid ($A^2$).

$R^4$ represents (as indicated above) hydrogen, alkyl, aryl or aralkyl, $R^4$ is preferably hydrogen, methyl or phenyl.

Examples of suitable chains are

—$(CH_2)_{1-4}$—

—$CH_2$—O—$CH_2$—, —$CH_2$—O—

—$CH_2$—S—$CH_2$—, —$CH_2$—S—

—$CH(CH_3)$—O—$CH_2$—, —$CH(CH_3)$—O—

—$(CH_2)_{1-2}$—C(O)—O—$CH_2$—, —C(O)—NH—

—$(CH_2)_4$—NH—C(O)—O—$CH_2$—

—$CH_2$—C(O)—NH—

—$CH_2$—C(O)—NH—$CH_2$—

—$CH_2$—C(O)—N($CH_3$)—$CH_2$—

—$CH_2$—C(O)—O—

—$CH_2$—NH—C(O)—$CH_2$—

—$CH_2$—NH—C(O)—O—

—$CH_2$—NH—C(O)—O—$CH_2$—

—CH₂—NH—C(O)—NH—
—(CH₂)₂—C(O)—NH—(CH₂)₂—
—(CH₂)₄—NH—C(O)—CH₂—
—(CH₂)₃—NH—C(O)—O—CH₂—

The chain contains preferably 1 to 5, more particularly 1 to 4 members.

Those compounds of formula I, according to the invention, are preferred, wherein R¹ is vinyl, aryl, heteroaryl, aralkyl, heteroaralkyl, arylvinyl, heteroarylvinyl, aryloxyalkyl, arylalkyloxy, di(arylalkyl)aminoalkyl or arylalkylaminoalkyl (wherein aryl is phenyl, mono-, di- or trisubstituted phenyl or naphthyl; the substituents of the phenyl group, independently of each other are halogen, trihalomethyl, alkoxy, alkyl or cyano; heteroaryl is indolyl, indolyl substituted in position 1 by alkyl or benzyl, pyridyl, pyrrolyl, imidazolyl or thienyl; and the alkyl or alkoxy group contains 1 to 3 carbon atoms);

A¹ is D- or L-alanine (Ala), (D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ(3,4)-Pro), D- or L-hydroxyproline (Pro(OH)) such as 3-hydroxyproline (Pro(3OH)) and 4-hydroxyproline (Pro(4OH)), D- or L-azetidin-2-carboxylic acid (Azt), D- or L-thioproline (Tpr), D- or L-aminoproline (Pro(NH₂)) such as 3-aminoproline (Pro(3NH₂)) and 4-aminoproline (Pro(4NH₂)), D- or L-pyroglutamic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Asn), D- or L-lysine (Lys), D- or L-arginine (Arg), D- or L-histidine (His), D- or L-ornithine(Orn), D- or L-hydroxy piperidine carboxylic acid such as 5-hydroxypiperidine-2-carboxylic acid, D- or L-mercaptoproline (Pro(SH)) such as 3-mercaptoproline (Pro(3SH)) and 4-mercaptoproline (Pro(4SH)), Tpr(O), Met(O), Tpr(O₂) or Met(O₂), and the geometric isomers thereof, whereby the hydroxy and amino groups contained therein may be protected by usual protective groups (e.g. acyl, carbamoyl or aralkyl (in particular benzyl));
and if B is group —A²—NR²R³

A² is a lipophilic amino acid which contains a phenyl-, mono-, di- or trisubstituted phenyl-, heteroaryl-, cyclohexyl- or cyclopentyl group or a mono- or di-$C_{1-3}$-alkylamino group, and this cyclic group or amino group is separated by a 1- to 8-membered chain from the backbone of the amino acid (whereby the substituents of the phenyl group independently of each other are halogen, trihalomethyl, alkoxy, alkyl, cyano or 1-pyrrolidinyl and the chain is defined as in claim 1) or A² is Leu, Ile, Nle, Val, Met or one of the groups

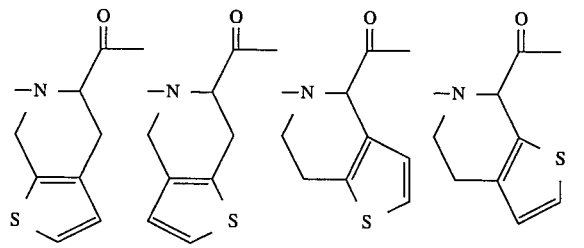

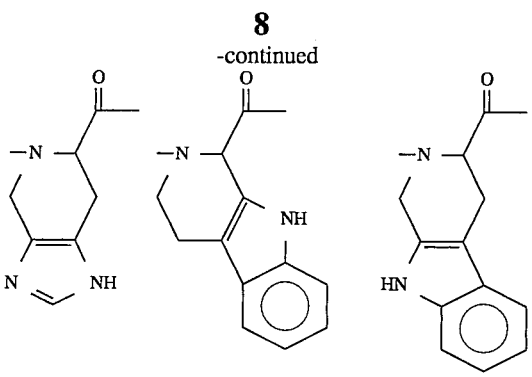

and

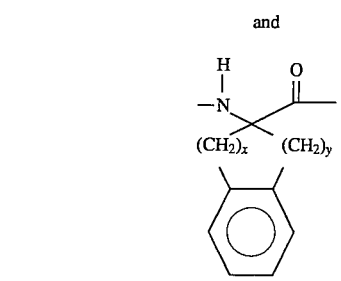

(wherein x and y independently of each other are 1 or 2);

R² and R³ independently of each other are alkyl, arylalkyl, heteroaryl or hydroxy (wherein aryl represents phenyl, mono-, di- or trisubstituted phenyl or naphthyl; the substituents of the phenyl group independently of each other denote halogen, trihalomethyl, alkoxy, alkyl or cyano; heteroaryl represents indolyl, pyridyl, pyrrolyl, imidazolyl or thienyl; and the alkyl or alkoxy groups contains 1 to 3 carbon atoms) or the group

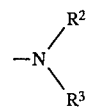

is a ring of general formula

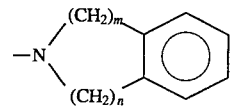

or

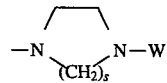

wherein m, n and s are defined as in claim 1 and W is the group

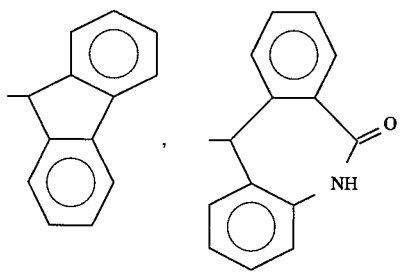

—(CH₂)₀₋₂-aryl, CH(aryl)₂, cyclopentyl or (CH₂)₀₋₂-cyclohexyl (wherein aryl represents phenyl, mono-, di- or trisubstituted phenyl or naphthyl; the substituents of the phenyl group independently of each other are halogen, trihalomethyl, alkoxy, alkyl or cyano).

Of the compounds, according to the invention, of formula Ia $$R^1—C(O)—A^1—A^2—NR^2R^3 \quad \text{Ia}$$

those are preferred wherein $R^1$ represents aryl, heteroaryl, aralkyl, heteroaralkyl, aryloxyalkyl, arylalkyloxy, di(arylalkyl)aminoalkyl (wherein aryl denotes phenyl or mono- or disubstituted phenyl; the substituents of the phenyl group independently of each other are halogen or alkoxy; heteroaryl denotes indolyl, indolyl or pyridyl substituted by alkyl or benzyl in position 1; and the alkyl or alkoxy group contains 1 to 3 carbon atoms; particularly

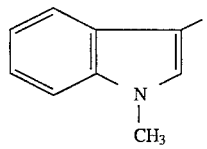

and/or $A^1$ is an amino acid which carries one or 2 polar functional group(s) in the side chain such as OH, COOH, $NH_2$, guanidine, $CONH_2$, SH; particularly wherein the functional group in the side chain of $A^1$ is OH and/or wherein $A^1$ is Pro, 4-hydroxyproline, 3-hydroxyproline, Ser, Thr, Trp(For) or Tyr; preferably 4-hydroxyproline with 2-S-configuration, particularly

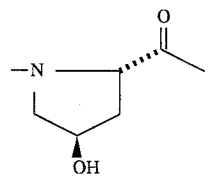

and/or wherein $A^2$ represents an acyclic or cyclic amino acid such as (O-benzyl)Ser, (O-subst. benzyl)Ser, (O-benzyl)Thr, cyclohexylalanine, homophenylalanine, 3-(1-pyrrolyl)-alanine, 3-(2,5-dimethyl-1-pyrrolyl)alanine, 3-(1-indolyl)alanine, 2-amino-4-(1-pyrrolyl)-butyric acid, 2-amino-5-(1-pyrrolyl)valeric acid, 2-amino-6-(1-pyrrolyl)caproic acid, Leu, Lys(Z), 3-(2-thienyl)alanine, 3-(3-benzothienyl)alanine, 3-(1-isoindolinonyl)alanine, (O-benzyl)Asp, (O-benzyl)Glu, Trp, (N-Me)Trp, His, 3-(2-thiazolyl)-alanine, or 3-dimethylamino-alanine, -(O-methyl) Tyr, 2-naphthylalanine,

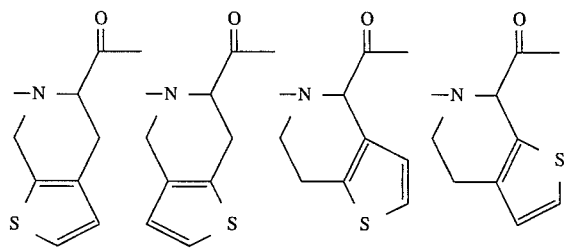

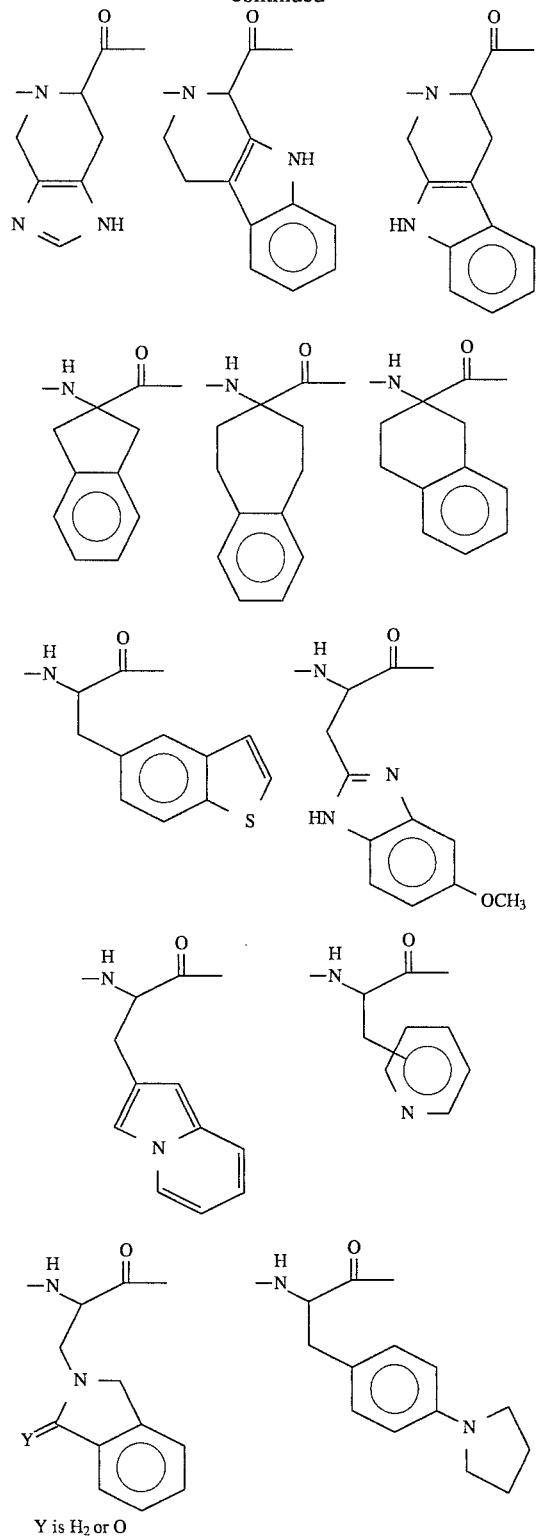

Y is $H_2$ or O

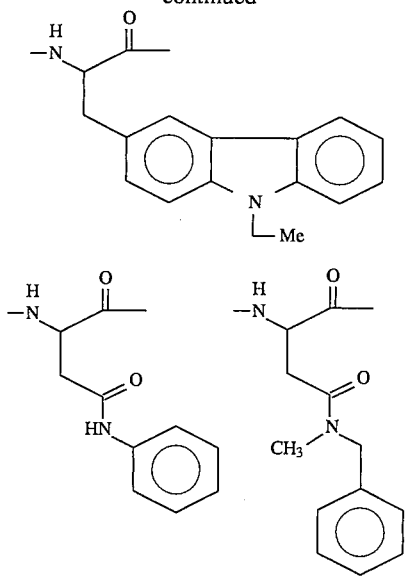

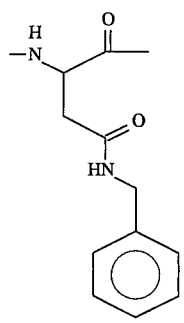

wherein the phenyl groups contained in the amino acids may be mono-, di- or trisubstituted and the substituents independently of each other are halogen, trihalomethyl, alkoxy, alkyl or cyano, the alkyl or alkoxy group contains 1 to 3 carbon atoms;

and wherein the above amino acids are preferably present in S-configuration;

special mention must be made of compounds wherein $A^2$

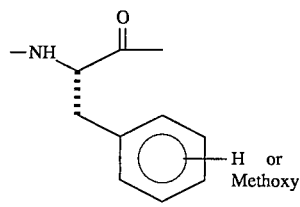

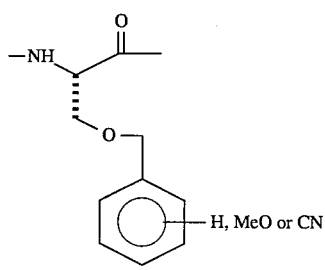

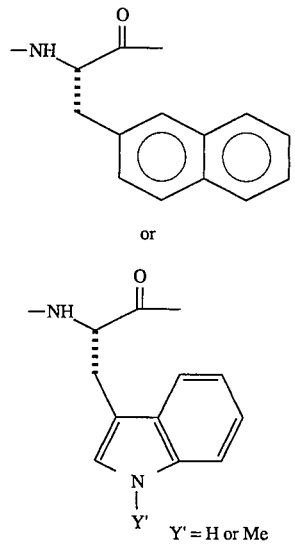

and/or wherein $R^2$ and $R^3$ independently of each other represent methyl, benzyl, phenethyl (wherein the phenyl groups contained therein are substituted by one or two methoxy groups) or pyridylmethyl;

preferably a compound wherein $R^2$ is methyl and $R^3$ is benzyl or alkoxybenzyl, more particularly wherein $R^3$ is alkoxybenzyl, preferably 2-methoxybenzyl; or wherein the group

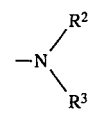

represents a ring

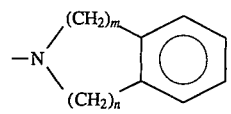

wherein m is 1 and n is 1 or 2;
or wherein the group

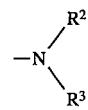

is a ring

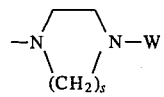

wherein s is 2 or 3 (preferably 2) and W is as hereinbefore defined;

preferably wherein W

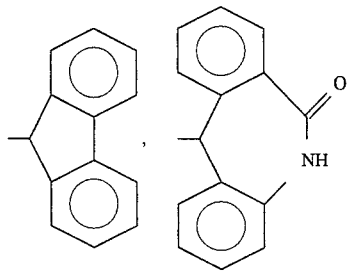

is cyclohexyl, phenyl or CH(phenyl)$_2$ wherein the phenyl groups are substituted;
wherein if W is phenyl, this is preferably monosubstituted by halogen, alkoxy, alkyl, cyano, hydroxy, nitro or alkylthio, particularly by methoxy, chlorine, methyl, ethyl, cyano, hydroxy, nitro or methylthio, preferably by methoxy, chlorine, methyl, cyano or methylthio, wherein the substituent of the phenyl group is preferably in position 2 and
if W represents the group —CH(phenyl)$_2$, the phenyl group is substituted by one halogen each, preferably by fluorine, wherein in the —CH(phenyl)$_2$ group the two phenyl groups are preferably substituted identically, preferably in p-position.

Of the compounds, according to the invention, of formula Ib

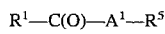

those are preferred wherein

R$^1$ represents aryl, heteroaryl, aralkyl, heteroaralkyl, aryloxyalkyl, arylalkyloxy, di(arylalkyl)aminoalkyl (wherein aryl represents phenyl or mono- or polysubstituted phenyl; the substituents of the phenyl groups independently of each other are halogen or alkoxy; heteroaryl denotes indolyl, indolyl or pyridyl substituted by alkyl or benzyl in position 1; and the alkyl or alkoxy group contains 1 to 3 carbon atoms); particularly

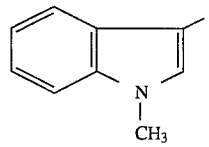

and/or

A$^1$ is an amino acid which carries one or 2 polar functional group(s) in the side chain such as OH, COOH, NH$_2$, guanidine, CONH$_2$, SH; particularly wherein
the functional group in the side chain of A$^1$ represents OH and/or wherein A$^1$ is Pro, 4-hydroxyproline, 3-hydroxyproline, Ser, Thr, Trp(For) or Tyr; preferably 4-hydroxyproline with 2-S-configuration, particularly

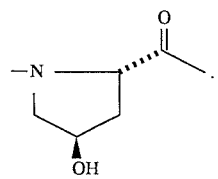

Of the compounds according to the invention, those are preferred wherein R$^5$ is a group of general formula II

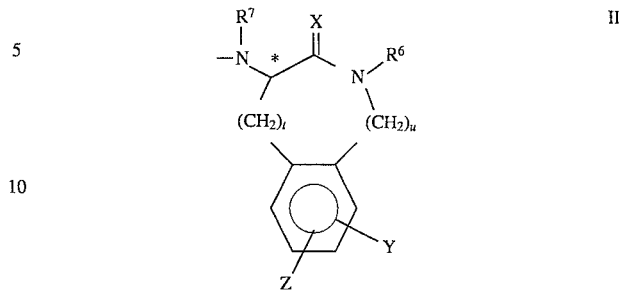

particularly those wherein t is one and u is zero or t is two and u is zero or t and u is one each, and R$^6$, R$^7$, X, Y and Z are specified as hereinbefore.

Special mention must be made of those compounds wherein
R$^6$ is benzyl or methoxybenzyl and/or wherein R$^7$ is hydrogen and/or wherein X is oxo and/or wherein Y and Z independently of each other represent methoxy, hydrogen, CF$_3$ or tert.butyl or together —(CH)$_4$—.

The above amino acids are preferably in S-configuration.

Test results of the compounds according to the invention:

The receptor affinity to the NK$_1$-receptor (substance P-receptor) was determined with cloned NK$_1$-receptors on human lymphoblastoma cells (IM-9), whereby the displacement of $^{125}$I-labelled substance P is measured. The IC$_{50}$-values thus obtained are:

Compound A: 60 nM
Compound B: 21 nM
Compound C: 90 nM
Compound D: 45 nM
Compound E: 6 nM
Compound F: 15 nM
Compound G: 1.7 nM

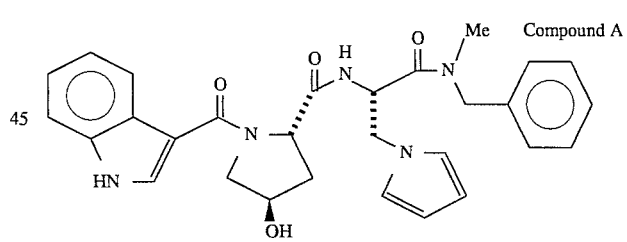

Compound A

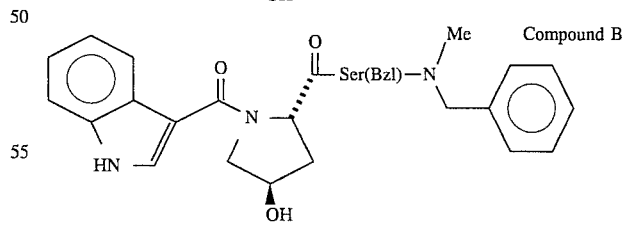

Compound B

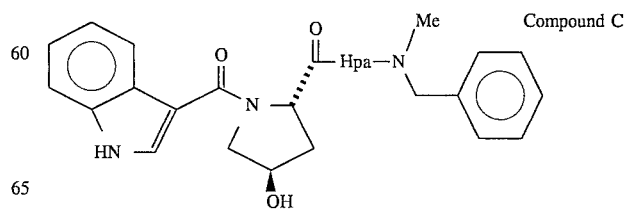

Compound C

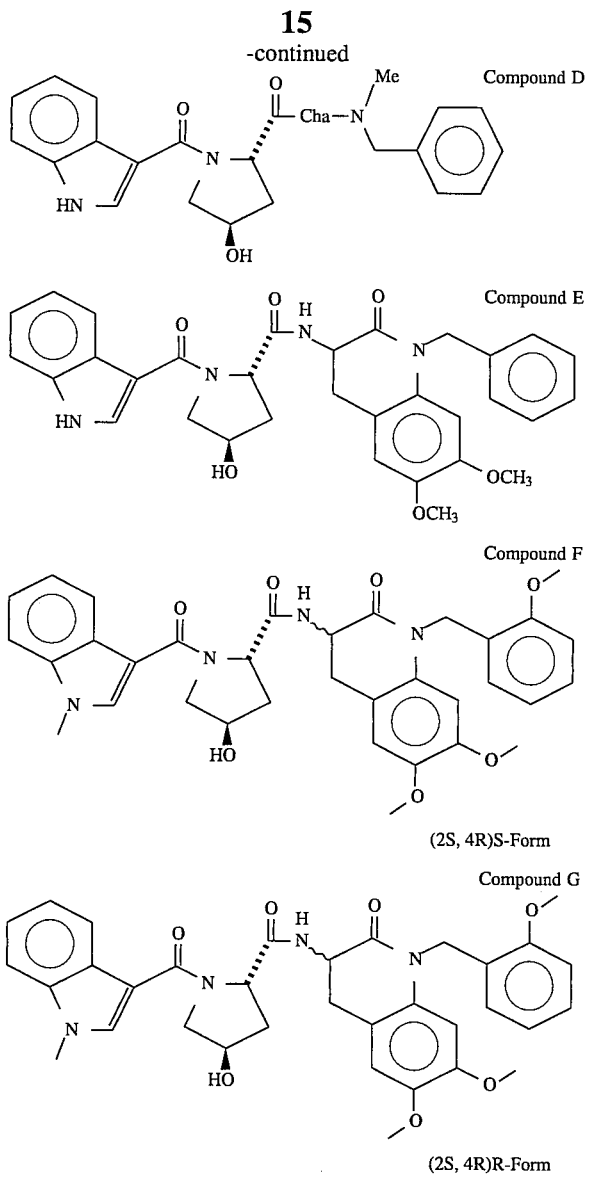

Compound D

Compound E

Compound F (2S, 4R)S-Form

Compound G (2S, 4R)R-Form

The compounds according to the invention are valuable neurokinin (tachykinin)-antagonists which have, in particular substance P-antagonism, but also neurokinin A- and neurokinin-B antagonistic properties. They are useful for treating and preventing neurokinin-receptive diseases such as respiratory tract diseases e.g. asthma, bronchitis, rhinitis, cough or expectoration as well as inflammatory eye diseases such as conjunctivitis, inflammatory skin diseases such as dermatitis and urticaria, other inflammatory diseases such as polyarthritis or osteoarthritis as well as painful conditions and vomiting.

The invention also relates to the use of the compounds according to the invention as drugs and pharmaceutical preparations containing these compounds. It is preferred if the compounds are used for human beings. They may be given intravenously, subcutaneously, intramuscularly, intraperitoneally, intranasally, inhalationally, transdermally, optionally assisted by iontophoresis or new enhancers, and orally.

For the parenteral administration, the compounds of formula I or the physiologically compatible salts thereof are placed in solution, suspension or emulsion, optionally with the substances normally used for this purpose such as solubilisers, emulsifiers or other excipients. The solubilisers used are for example: water, physiological sodium chloride solutions or alcohols such as ethanol, propanediol or glycerin, sugar solutions such as glucose or mannitol solutions or else a mixture of different solubilisers.

Furthermore, the compounds may be administered by implants, for example of polylactide, polyglycolide or polyhydroxybutyric acid or intranasal preparations.

The compounds may be prepared using generally known methods of amino and peptide chemistry, by condensing, step by step, the relevant amino acids or peptide derivative part sequences, carboxylic acids and amines and isolating the compound thus obtained in free form or in the form of the desired salt.

The dipeptide derivatives of formula Ia

$R^1-C(O)-A^1-A^2-NR^2R^3$  Ia may be synthesised from the parts $R^1$—COOH, H—$A^1$—OH, H—$A^2$—OH and HN($R^3$)$R^2$, whereby the sequence of the couplings may be from right to left, from left to right or by coupling the units $R^1$—CO—$A^1$—OH and H—$A^2$—N($R^3$)$R^2$ (fragment couplings).

The compounds according to the invention may be prepared using generally known methods of peptide chemistry such as described in "Houben-Weyl, Methoden der organischen Chemie, Vol. 15/2", or using the solid phase peptide synthesis (e.g. R. C. Sheppard, Int. J. Pept. Prot. Res., 21, 118 [1983]) or similar known methods. Here, the relevant amino acids or amino acid partial sequences are condensed step by step and the resultant peptides are isolated in free form or in the form of the desired salts. The amino protective groups used as those described in "Houben-Weyl, Methoden der organischen Chemie, Vol. 15/1", whereby the benzyloxycarbonyl group (Z) is preferred in conventional syntheses and the fluorenylmethoxycarbonyl group (Fmoc) in solid phase syntheses. In the case of the conventional synthesis the side chain of the arginine was protected by protonation, in the case of the solid phase synthesis, the Mtr-group was used. In the solid phase peptide synthesis the following amino acids with protected side chains were for example used: Lys(Boc), His(Bum), Ser(tBu) and Asp(tBu). The specific synthesis conditions are apparent from the following Examples.

For the synthesis of the compounds of general formula I using the solid phase synthesis, those dipeptide carboxylic acids are initially synthesised which are reacted in solution to form dipeptide amides. The following anchor groups are suitable 1. Benzylester (G. Barang, R. B. Merrifield, Peptides 2, 1 (1980) Eds. E. Gross, J. Meienhofer, Academic Press, New York)
2. PAM-Anker (R. B. Merrifield, J. Am. Chem. Soc. 85, 2149 (1966))
3. Wang-Anker (S.-S. Wang, J. Am. Chem. Soc. 95, 1328 (1973))
4. SASRIN-Anker (M. Mergler, R. Tanner, J. Gostuli, P. Grogg, Tetrah. Lett. 29, 4005 (1988)).

For preparing the compounds of formula Ib

$R^1-C(O)-A^1-R^5$  Ib the components $R^1$—COOH, the amino acid H—$A^1$—OH and the amine H—$R^5$ are bonded to one another. Optionally, the carboxylic acid of $R^1$—COOH may first be coupled with a suitably protected form of H—$A^1$—OH and concentrated with the amine H—$R^5$ using the protective group cleavage, or the suitably protected amino acid H—A¹—OH may first be reacted with H—R⁵ and this product may be coupled with R¹—COOH after deprotection.

The basic bodies of the amines H—R⁵ may be obtained using known methods:

if H—R⁵ is

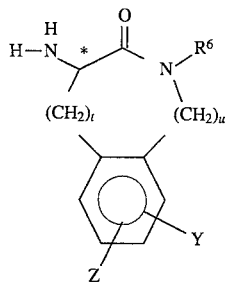

IIa with t=1 and u=0 and R⁶, Y and Z are as hereinbefore described, the preparation is carried out using known methods as described by A. L. Davis et al., J. Med. Chem. 18, 752 (1975) or H. Merz, DE 38 23 576 (C.A. 114 (21), 207 052 m). The introduction of the group R⁶ into a compound of general formula XI is carried out by the reaction with NaH and BrR⁶. This reaction may take place by either using a protective group (Sch) on the exocyclic N or not.

This preparation may be demonstrated by the following reaction scheme:

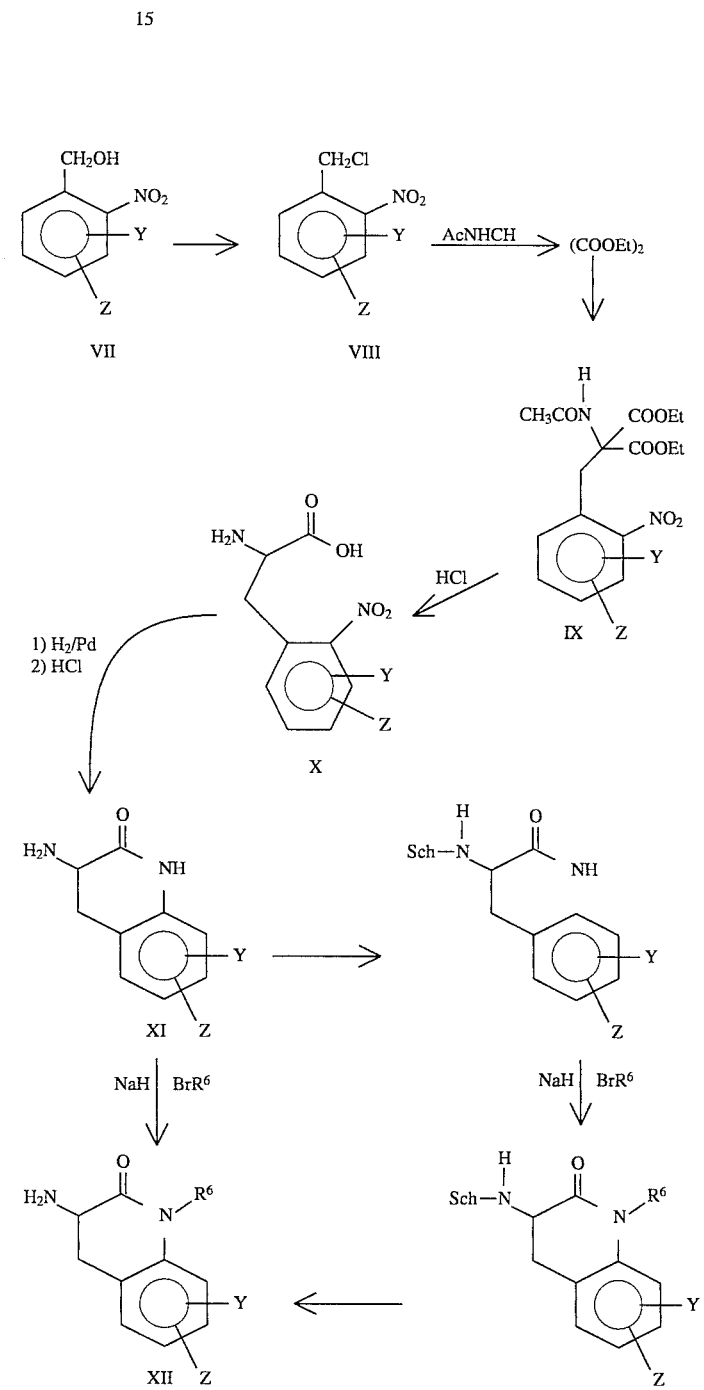

Suitable protective groups (Sch) are base-stable protective groups such as the Boc-group.

In order to prepare a compound of general formula XI, a compound of general formula X is reduced under cyclisation (e.g. analogous to the method described by A. L. Davis et al. (J. Med. Chem. 9, 826 (1966)) by means of Pd-Mohr).

The compound X may be prepared from the correspondingly substituted 1-nitrobenzylalcohol (VIII) and via the intermediary stages VIII and IX (by halogenation with e.g. $SOCl_2$ and subsequent reaction with acetamidomalonic acid diethylester according to (J. Med. Chem. 9, 828 (1966)).

An amine $H-R^5$ of general formula IIb

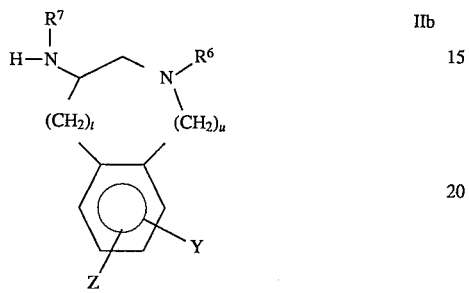

IIb wherein t=1 and u=0 and $R^6$, Y and Z are as specified hereinbefore for formula IIa may be prepared by reduction of a corresponding compound IIa by means of e.g. $LiAlH_4$.

For preparing a compound IIa, wherein t=u=0 and $R^6$, Y and Z are as specified hereinbefore, the method according to A. L. Davis et al., J. Med. Chem. 16, 1043 (1973) is suitable. Here, starting from α-bromo-o-nitrophenylacetic acid methylester, the phthalimido group is introduced and after cleavage of the protective groups and the reduction of the nitro group, the cyclisation takes place to form (substituted or unsubstituted) 3-amino-2-indolinone:

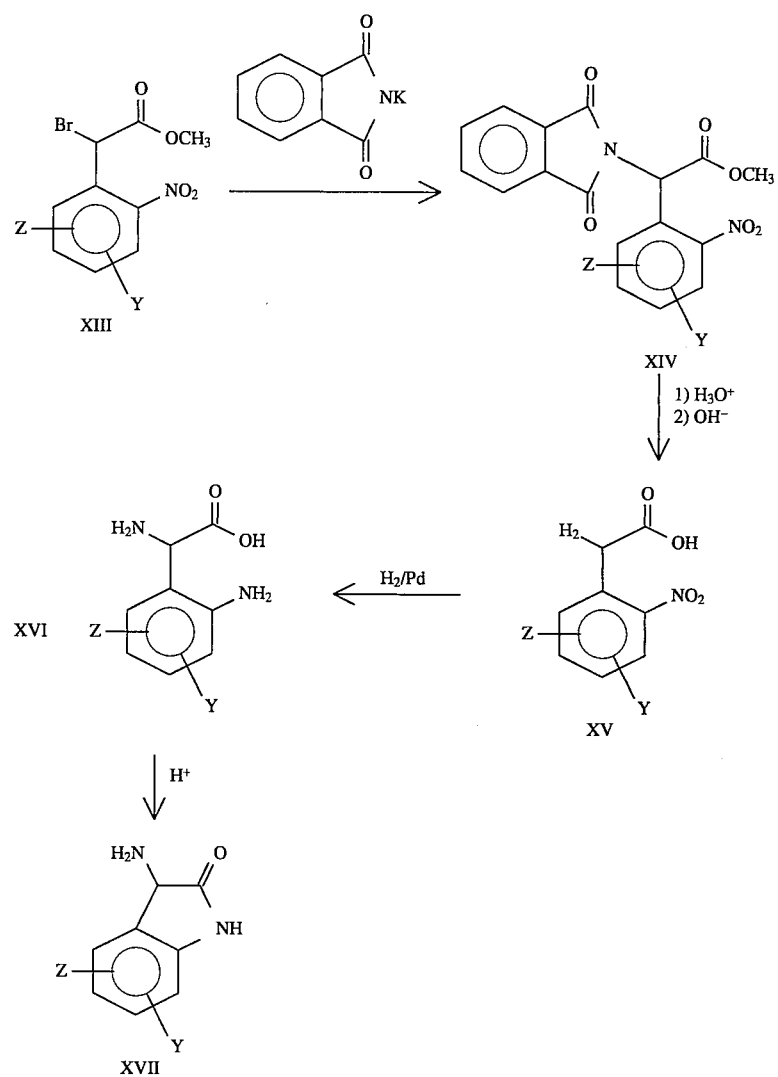

The introduction of $R^6$ and reduction to form the analogous compound of general formula IIb may be carried out as indicated above.

The preparation of compound IIa with t=2, u=0, wherein $R^6$, Y and Z is as defined above may be summarised by the following reaction scheme:

The preparation of compound IIa with t=u=1, wherein $R^6$, Y and Z is as defined above, may be carried out as follows: unsubstituted or substituted phthaloylphenylalanine is coupled with the amine $H_2N$—$R^6$ and then cyclised with formaldehyde in a reaction of the Pictet-Spengler kind.

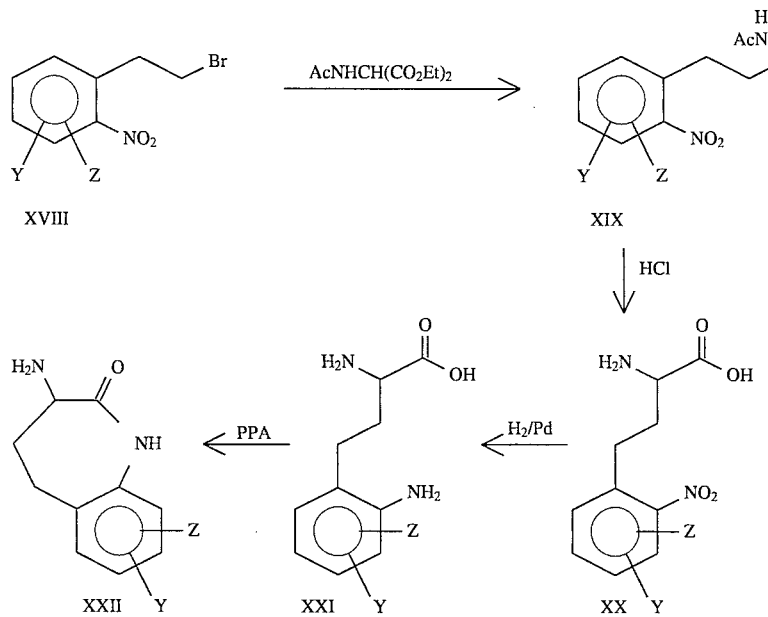

The introduction of $R^6$ and reduction to form the analogous compound IIb may be carried out as indicated above.

When using this preparation method, the correspondingly substituted 2-(2-nitrophenyl)-ethylbromide (XVIII) may be reacted with acetamidomalonic acid diethylester to form compound XIX and then XX, analogously to the methods described above.

The reduction of compound XX to form compound XXI may be carried out under pressure in a solution of MeOH and water, for example by hydrogen in the presence of Pd-Mohr. The cyclisation to prepare compound XXII may be carried out by polyphosphoric acid whilst stirring and heating.

Finally, the phthaloyl group is cleaved off, for example by treating with hydroxylamine:

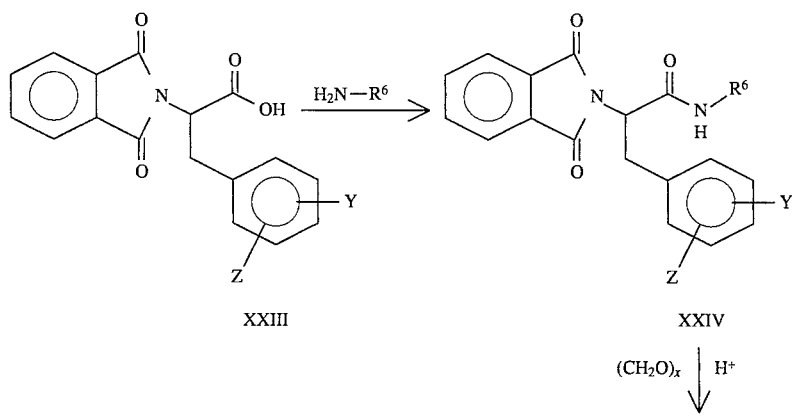

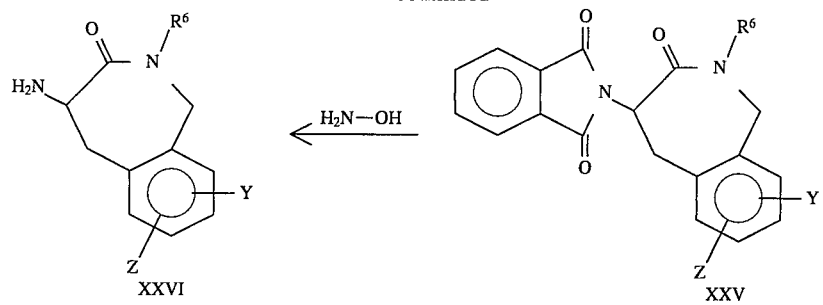

The reduction to form the analogous compound of general formula IIb may be carried out as indicated above.

The preparation of an amine $HR^5$ of general formula IIIa

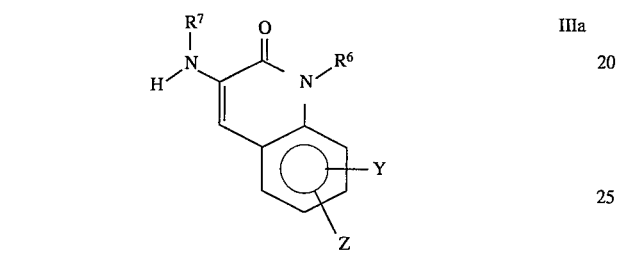

wherein $R^6$, Y and Z are as defined above may be carried out according to G-Leclerc et al., J. Med. Chem. 29, 2427 (1986). For this purpose, substituted or unsubstituted 3-bromoquinoline is first converted into the corresponding N-oxide, then transposed to the quinolin-2-one and finally the amino group is introduced with ammonium under pressure (in the carrier tube):

The preparation of a compound $HR^5$ of general formula IVa

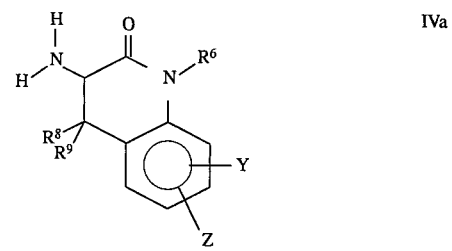

wherein $R^6$ is as defined above and $R^8$ represents hydroxy and $R^9$ is hydrogen, may be carried out according to R. Weichert, Arkiv Kemi 25, 231 (1966). Here, acetaminomalonic acid monoethylether is reacted with substituted or unsubstituted 2-nitrobenzaldehyde, finally it is hydrolysed, the nitro group is reduced and finally the cyclisation is carried out:

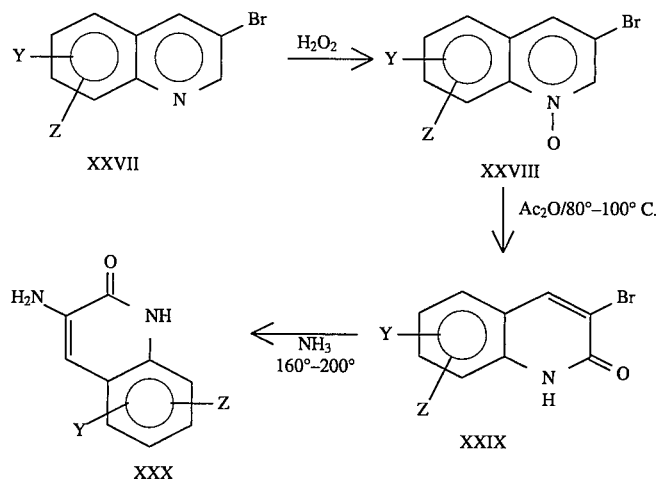

The introduction of the substituents $R^6$ may be carried out as described above with respect to compound IIa.

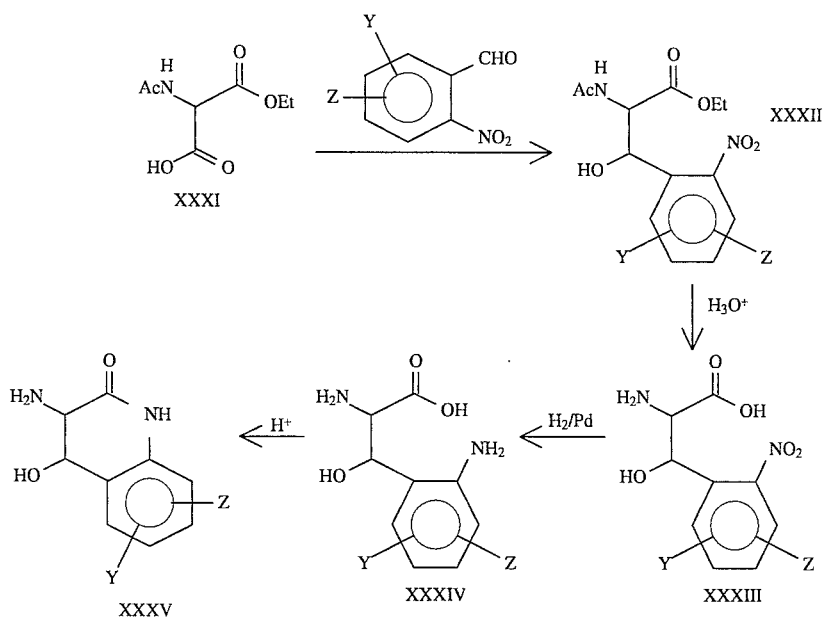

The introduction of $R^6$ is carried out as described above.

In order to prepare a compound IVa wherein $R^9$ represents $(C_{1-5})$alkoxy, phenyl-$(C_{1-5})$alkyloxy, naphthyl-$(C_{1-5})$alkyloxy or $(C_{1-4})$alkylcarbonyl or wherein $R^8$ and $R^9$ both represent oxygen or —$OCH_2CH_2O$—, the above compound IVa wherein $R^8$ represents hydrogen and $R^6$ represents hydroxy, may be reacted as follows:

a) for preparing a compound IVa, wherein $R^9$ is alkyloxy, phenyl or naphthylalkyloxy: etherication according to Williamson;

b) for preparing a compound IVa, wherein $R^9$ is alkylcarbonyl; reaction with the corresponding acid anhydride;

c) for preparing a compound IVa, wherein $R^8$ and $R^9$ both represent oxygen: oxidation according to e.g. Oppenauer;

d) for the preparation to form compound IVa, wherein $R^8$ and $R^9$ both represent —$OCH_2CH_2O$—: reaction of the keto compound obtained according to (c) with ethyleneglycol.

In order to prepare amines of general formula H—$R^5$, wherein $R^7$ is alkyl, the compounds of general formula IIa, IIb, IIIa and IVa are alkylated. This alkylation may be carried out by protecting the exocyclic N initially by e.g. trifluoroacetyl, carrying out the alkylation with e.g. alkylbromide and then cleaving the protective group by e.g. hydrolysis.

Pharmaceutical Preparations:

Injection solution

- 200 mg active substance*
- 1.2 mg potassium dihydrogen phosphate = $KH_2PO_4$ } (buffer)
- 0.2 mg sodium dihydrogen phosphate = $NaH_2PO_4 \cdot 2H_2O$
- 94 mg sodium chloride
  or
- 520 mg glucose } (isotonic)
- 4 mg albumin (protease protection)
- q.s. sodium hydroxide solution } to pH 6
- q.s. hydrochloric acid
- to 10 ml water for injection purposes Injection solution

- 200 mg active substance*
- 94 mg sodium chloride
  or
- 520 mg glucose
- 4 mg albumin
- q.s. sodium hydroxide solution } to pH 9
- q.s. hydrochloric acid
- to 10 ml water for injection purposes Lyophilisate

- 200 mg active substance*
- 520 mg mannitol (isotonic/structure builders)
- 4 mg albumin Solvent 1 for lyophilisate

- 10 ml water for injection purposes

Solvent 2 for lyophilisate

- 20 mg Polysorbat ®80 = Tween ®80 (surface-active substance)
- 10 ml water for injection purposes

*Active substance: compounds according to the invention, for example the compound of Example 1 or 201.
Dosage for human beings of 67 kg: 1 to 500 mg

EXAMPLE 1

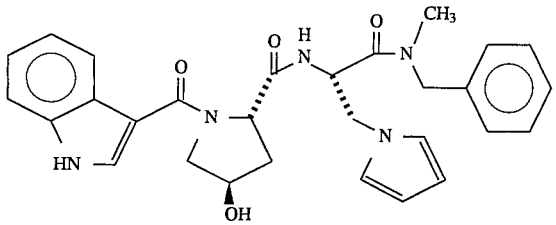

Preparation of Z-Pal-OMe 21.45 g of L-Z-(3-amino)alanine-methylester (74 mMol) are dissolved in 590 ml of ethyl acetate and 590 ml of water, mixed with 9.6 ml of 2,5-dimethoxytetrahydrofuran (74 mMol) and stirred for 23 hours at ambient temperature. The organic phase is separated, washed twice with saturated NaHCO$_3$ solution and twice with 10% NaCl solution, dried and concentrated to dryness after filtering. The residue is taken up in a 1:1 mixture of ether and petroleum ether 40/80 and chromatographed over a short silica gel column. After concentration 12.5 g of Z-Pal-OMe is obtained as colourless oil from the eluant.

$[\alpha]_D^{20}$ (MeOH)=−26.8°.

Preparation of Z-Pal-OH 5.5 g of Z-Pal-OMe (18.2 mMol) are dissolved in 100 ml of acetonitrile, mixed with 20 ml of 1N NaOH and stirred for 3 hours at ambient temperature. The mixture is neutralised by adding 20 ml of 1N NaOH, the solvent is largely removed on the rotary evaporator and the solid residue is mixed with ice cold water. After suction filtering the mixture is washed with a little water and the residue is dried in the desiccator whereby Z-Pal-OH is obtained in the form of white crystals. M.p.: 82° C.; $[\alpha]_D^{20}$ (MeOH)=−9.4°.

Preparation of Z-Pal-N (Me) Bzl 2.5 g of Z-Pal-OH (8.7 mMol) are dissolved in 50 ml of THF, mixed with 1.55 g CDI (9.5 mMol), stirred for 45 minutes at ambient temperature, then mixed with 1.12 ml of N-methyl-benzylamine (8.7 mMol) and stirred for a further 64 hours at ambient temperature. The reaction mixture is concentrated on the rotary evaporator, the residue is taken up in ethyl acetate, extracted once with cold water and once with 10% NaCl solution. The organic phase is filtered, concentrated and chromatographed over a silica gel column by means of ether as eluant. Z-Pal-N(Me)Bzl is obtained as colourless oil from the eluant. $[\alpha]_D^{20}$ (MeOH )=−0.3°.

Preparation of H-Pal-N (Me) Bzl 2.68 g of Z-Pal-N(Me)Bzl (6.85 mMol) are dissolved in 30 ml of MeOH and after adding 0.3 g of Pd-carbon hydrogenated for 5 hours at ambient temperature and 5 bar. Then, the mixture is filtered, the filtrate is concentrated on the rotary evaporator, the residue is dissolved in ether, filtered and the filtrate is again concentrated. H-Pal-N(Me)Bzl is obtained as a light green oil. $[\alpha]_D^{20}$ (MeOH)=+38.8°.

Preparation of H-Hyp-Pal-N(Me)Bzl 1.52 g of H-Pal-N(Me)Bzl (5.9 mMol), 1.37 g of Boc-(2S, 4R)-hydroxy-proline (5.9 mMol) and 0.91 g of HOBt. H$_2$O (5.9 mMol) are dissolved in 120 ml of THF, cooled down to 3° C. and mixed with 1.83 g of DCCI (8.9 mMol). The mixture is stirred for 2 hours at 3° C. and for a further 13 hours at ambient temperature, then it is filtered off from the resultant DCH, the filtrate is concentrated and the residue is taken up in acetonitrile. It is filtered again, the filtrate is concentrated, taken up in ethyl acetate and the organic phase is washed twice with saturated NaHCO$_3$ solution and three times with 10% NaCl solution. After drying by means of MgSO$_4$ and chromatography over silica gel with ethyl acetate as eluant Boc-Hyp-Pal-N(Me)Bzl is obtained as a white firm foam.

The resultant Boc-Hyp-Pal-N(Me)Bzl is dissolved in 40 ml of CH$_2$Cl$_2$ and mixed with 20 ml of TFA whilst cooling with ice. The mixture is stirred for 15 minutes at ambient temperature, concentrated on the rotary evaporator, the residue is taken up in ethyl acetate and extracted twice with saturated NaHCO$_3$ solution. The aqueous phase is extracted successively with ethyl acetate and CH$_2$Cl$_2$. All the organic phases are united, dried with MgSO$_4$, concentrated and the residue is chromatographed over silica gel by means of acetonitrile/water/MeOH (4:1:1). 0.39 g of H-Hyp-Pal-N(Me)Bzl is obtained as a highly viscous, colourless oil. $[\alpha]_D^{20}$ (MeOH)=−38.1°.

Preparing 3-indolylcarbonyl-Hyp-Pal-N(Me)Bzl 0.32 g of H-Hyp-Pal-N(Me)Bzl (0.9 mMol) are dissolved in 30 ml of CH$_2$Cl$_2$, mixed with 0.52 ml of bis(trimethylsilyl)acetamide (2.1 mMol), stirred for 40 minutes at ambient temperature, mixed with 0.19 g of indol-3-carboxylic acid chloride (1 mMol) at 0° C., stirred for a further 2 hours at 0° C. and finally for 1 hour at ambient temperature. The reaction mixture is concentrated on the rotary evaporator, the residue is taken up in 25 ml of THF and 7 ml of 1N NaOH and neutralised by adding 7 ml of 1N HCl after stirring for 1 hour. The THF is distilled off on the rotary evaporator, the resultant aqueous phase is extracted twice with ethyl acetate, the combined ethyl acetate phases are filtered and the filtrate is concentrated. After chromatography over silica gel with ethyl acetate/MeOH (9:1) as eluant, 3-indolylcarbonyl-Hyp-Pal-N(Me)Bzl is obtained as a white solid material. M.p.: 112°–116° C. $[\alpha]_D^{20}$ (MeOH) =−124.4°.

The following Tables list further compounds which may be prepared analogously.

TABLE 1

[Structural formula showing indole-C(=O)-A¹-A²-N(R²)(R³)]

| No. | A¹ | A² | -N(R²)(R³) |
|-----|-----|-----|-----|
| 1 | 4-hydroxy-pyrrolidine-2-carbonyl (Hyp) | N-methyl-(1H-pyrrol-1-ylmethyl)-amino acid residue | -N(Me)Bzl |
| 2 | Hyp | Ser(Bzl) | -N(Me)Bzl |
| 3 | Hyp | Hpa | -N(Me)Bzl |
| 4 | Hyp | Cha | -N(Me)Bzl |
| 5 | Hyp | 2-amino-4-(1H-pyrrol-1-yl)butanoyl | -N(Me)Bzl |
| 6 | Hyp | 2-amino-5-(1H-pyrrol-1-yl)pentanoyl | -N(Me)Bzl |

TABLE 1-continued

| No. | A¹ | A² | −N(R²)(R³) |
|---|---|---|---|
| 7 | Hyp | −NH−CH(−(CH₂)₃−N-pyrrolyl)−C(O)− | −N(Bzl)₂ |
| 8 | Hyp | −NH−CH(−(CH₂)₃−N-pyrrolyl)−C(O)− | N-(9-fluorenyl)piperazinyl |
| 9 | Hyp | −NH−CH(−(CH₂)₃−N-pyrrolyl)−C(O)− | isoindolinyl |
| 10 | Hyp | −NH−CH(−(CH₂)₃−N-pyrrolyl)−C(O)− | −N(Me)Bzl |
| 12 | Hyp | −NH−CH(−CH₂-(2-thienyl))−C(O)− | −N(Me)Bzl |

TABLE 1-continued

[Structure: indole-C(=O)-A¹-A²-N(R²)(R³); with -N(R²)(R³) shown separately]

| No. | A¹ | A² | -N(R²)(R³) |
|---|---|---|---|
| 13 | Hyp | -NH-CH(CH₂-thiophen-2-yl)-C(=O)- | -N(Me)CH₂CH₂Ph |
| 14 | Hyp | 4,5,6,7-tetrahydrothieno[2,3-c]pyridin-5-yl acetyl | -N(Me)Bzl |
| 15 | Thr | 4,5,6,7-tetrahydrothieno[2,3-c]pyridin-5-yl acetyl | -N(Me)Bzl |
| 16 | Hyp | 4,5,6,7-tetrahydrothieno[2,3-c]pyridin-5-yl acetyl | 1,2,3,4-tetrahydroisoquinolin-2-yl |
| 17 | Hyp | -NH-CH(CH₂-benzothiophen-3-yl)-C(=O)- | -N(Me)Bzl |
| 20 | Hyp | —Asp—<br>\|<br>Bzl | -N(Me)Bzl |
| 22 | Hyp | —Asp—<br>\|<br>Bzl | -N(OH)Bzl |

TABLE 1-continued
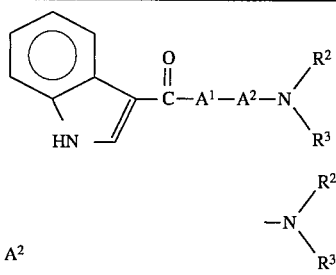
| No. | A¹ | A² | -N(R²)(R³) |
|---|---|---|---|
| 23 | Hyp | —Glu(Bzl)— | —N(Me)Bzl |
| 24 | Hyp | —Glu(Bzl)— |  |
| 25 | Hyp |  | —N(Me)Bzl |
| 26 | Hyp |  | —N(Me)Bzl |
| 27 | Hyp | 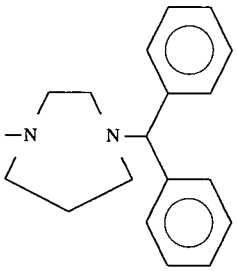 | —N(Bzl)₂ |
| 28 | Hyp | 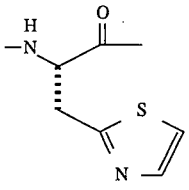 | —N(Me)Bzl |

TABLE 1-continued
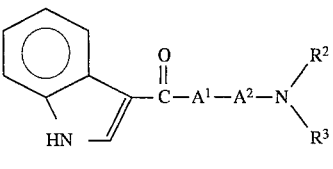
| No. | A¹ | A² | −N(R²)(R³) |
|---|---|---|---|
| 29 | Hyp | 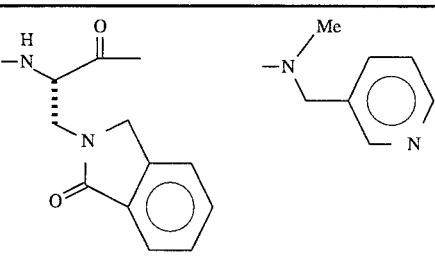 | 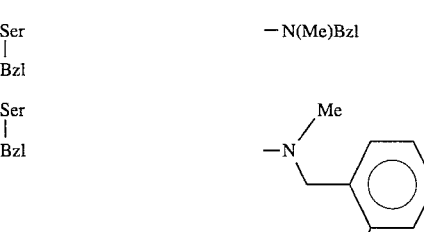 |
| 30 | Pro | Ser\|Bzl | —N(Me)Bzl |
| 31 | Hyp | Ser\|Bzl | 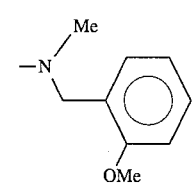 |
| 32 | Hyp | Ser\|Bzl | 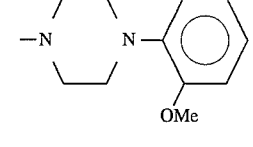 |
| 33 | Hyp | Ser\|Bzl | 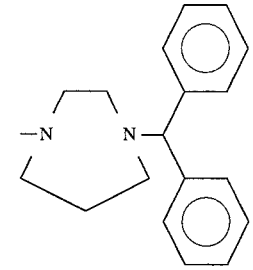 |
| 34 | Hyp | D—Ser\|Bzl | —N(Me)Bzl |
| 35 | Hyp | Ser—(4-Cl-Bzl)  | —N(Me)Bzl |
| 36 | Hyp | Ser—(4-Cl-Bzl) 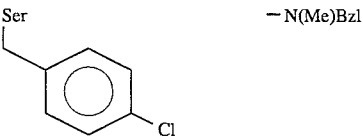 |  |

TABLE 1-continued
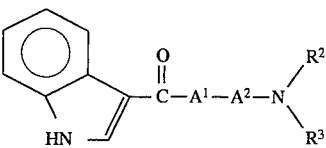
| No. | A¹ | A² | -N(R²)(R³) |
|-----|-----|-----|-----|
| 37 | Hyp | Ser(4-Cl-Bzl) | 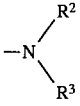 |
| 38 | Hyp | Leu | —N(Me)Bzl |
| 39 | Hyp | Thr(Bzl) | —N(Me)Bzl |
| 40 | Hyp | Thr(Bzl) | 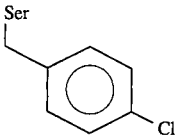 |
| 41 | Hyp | Lys(Z) | 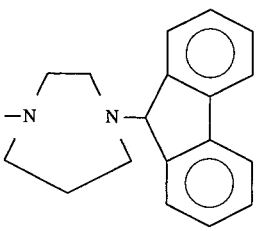 |
| 42 | Hyp | 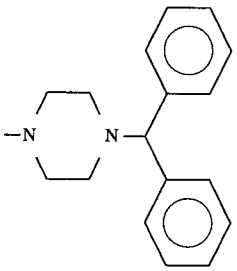 | —N(Me)Bzl |
| 43 | Hyp | 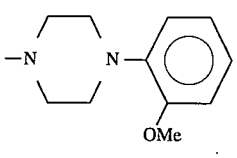 | 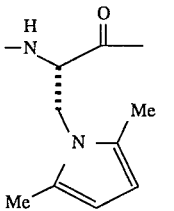 |

TABLE 1-continued

| No. | A¹ | A² | −NR²R³ |
|-----|-----|-----|-----|
| 44 | Hyp | −NH−CH(CH₂−(2,5-dimethylpyrrol-1-yl))−C(=O)− | −NH−CH₂−(3,4-dimethoxyphenyl) |
| 45 | Hyp | −NH−CH(CH₂−(2,5-dimethylpyrrol-1-yl))−C(=O)− | −N(piperazinyl)−(2-methoxyphenyl) |
| 46 | Hyp | −NH−CH(CH₂−(indol-1-yl))−C(=O)− | −N(Me)Bzl |
| 47 | Hyp | Lys(Z) | −N(CH₃)CH₂−phenyl |
| 48 | Hyp | −NH−CH(CH₂−(1-methylindol-3-yl))−C(=O)− | −N(Me)Bzl |

TABLE 2

Structure: Indole-3-carbonyl-A¹-A²-N(R²)(R³), with R⁴ on indole N.

| No. | R⁴ | A¹ | A² | -N(R²)(R³) |
|-----|-----|-----|-----|-----|
| 49 | CH₃ | Hyp | (thiophene-fused piperidinyl methyl ketone substituent) | -N(Me)Bzl |
| 50 | Bzl | Hyp | (NH-CH(CH₂N(Me)₂)-C(O)-Me) | -N(Me)Bzl |
| 51 | Me | Hyp | Trp | -N(Me)Bzl |
| 52 | Me | Hyp | His | -N(Me)Bzl |
| 53 | CH₃ | Hyp | Lys(Z) | -N(Me)Bzl |

TABLE 2-continued

| No. | R⁴ | A¹ | A² | -N(R²)(R³) |
|-----|-----|-----|-----|-----|
| 54 | CH₃ | Hyp | (NH-CH(CH₂-pyrrol-1-yl)-C(O)-) | -N(Me)Bzl |
| 55 | CH₃ | Hyp | Ser(Bzl) | -N(Me)Bzl |
| 55a | CH₃ | Hyp | Ser(p-CN—Bzl) | -N(Me)(CH₂-2-OCH₃-C₆H₄) |
| 56 | CH₃ | Hyp | Hpa | -N(Me)Bzl |
| 57 | CH₃ | Hyp | Cha | -N(Me)Bzl |

TABLE 3

Structure: R¹-C(O)-A¹-A²-N(R²)(R³)

| No. | R¹ | A¹ | A² | -N(R²)(R³) |
|-----|-----|-----|-----|-----|
| 58 | 3,4-dimethoxy-phenyl (ethyl-substituted) | Hyp | Hpa | -N(Me)Bzl |
| 59 | 4-bromophenyl | Hyp | (NH-CH(CH₂CH₂-pyrrol-1-yl)-C(O)-) | -N(Me)Bzl |

TABLE 3-continued
R¹—C(=O)—A¹—A²—N(R²)(R³)
| No. | R¹ | A¹ | A² | —N(R²)(R³) |
|---|---|---|---|---|
| 60 | 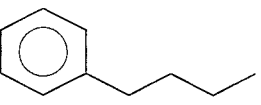 | Hyp | 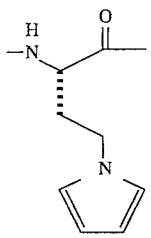 | —N(Me)Bzl |
| 61 | 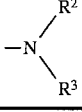 | Hyp | 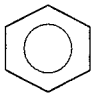 | —N(Me)Bzl |
| 62 | 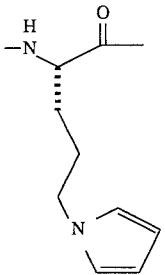 | Hyp | 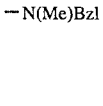 | —(N(Me)Bzl |
| 65 | 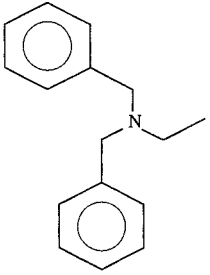 | Hyp | Glu\|Bzl | —N(Me)Bzl |
| 66 | 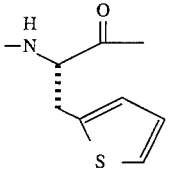 | Hyp | 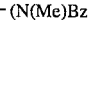 | —N(Me)Bzl |
| 67 | 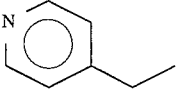 | Hyp |  | —N(Me)Bzl |

TABLE 3-continued $$R^1-\overset{\overset{O}{\|}}{C}-A^1-A^2-\overset{R^2}{\underset{R^3}{N}}$$

| No. | R¹ | A¹ | A² | $-N\overset{R^2}{\underset{R^3}{}}$ |
|---|---|---|---|---|
| 68 | phenylbutyl | Hyp | Ser<br>\|<br>Bzl | —N(Me)Bzl |
| 69 | 2-ethylpyridine | Hyp | Ser—(4-chlorobenzyl) | —N(Me)Bzl |
| 70 | phenylbutyl | Hyp | Lys<br>\|<br>Z | —N-piperazinyl-(2-methoxyphenyl) |
| 71 | phenylbutyl | Hyp | Lys<br>\|<br>Z | —N(Me)Bzl |
| 72 | (2-propenyl)aniline | Hyp | Lys(N-pyrrolyl) | —N(Me)Bzl |

TABLE 4
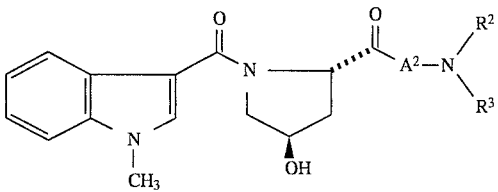
| No. | A² | -N(R²)(R³) |
|---|---|---|
| 73 | 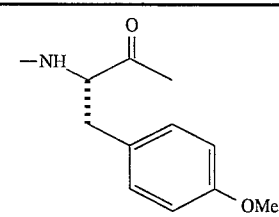 | 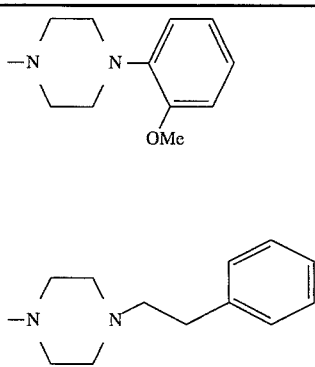 |
| 74 | 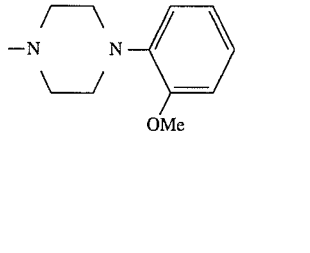 | 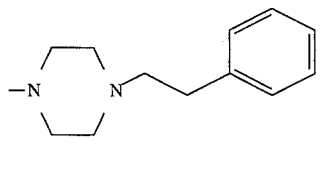 |
| 75 | 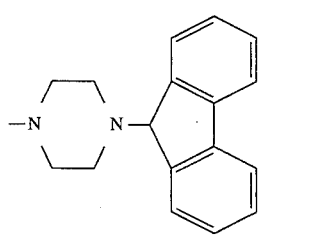 | |

TABLE 4-continued

| No. | A² | –N(R²)(R³) |
|---|---|---|
| 78 | –NH–CH(CH₂–O–CH₂–C₆H₅)–C(O)–CH₃ | piperazinyl–(4-OMe-C₆H₄) |
| 79 | –NH–CH(CH₂–O–CH₂–C₆H₅)–C(O)–CH₃ | piperazinyl–CH₂–(3,4-methylenedioxy, ethylene bridge)–C₆H₃ |
| 80 | –NH–CH(CH₂–C₆H₄–OMe)–C(O)–CH₃ | piperazinyl–CH₂–(3,4-methylenedioxy, ethylene bridge)–C₆H₃ |
| 81 | –NH–CH(CH₂–C₆H₄–OMe)–C(O)–CH₃ | piperazinyl–(4-OMe-C₆H₄) |
| 82 | –NH–CH(CH₂–C₆H₄–OMe)–C(O)–CH₃ | piperazinyl–(4-NO₂-C₆H₄) |

TABLE 4-continued

| No. | A² | –N(R²)(R³) |
|---|---|---|
| 83 | –NH–CH(CH₂–O–CH₂–C₆H₅)–C(=O)–CH₃ | piperazin-1-yl-(4-nitrophenyl) |
| 84 | –NH–CH(CH₂–O–CH₂–C₆H₅)–C(=O)–CH₃ | 4-(9H-fluoren-9-yl)piperazin-1-yl |
| 85 | –NH–CH(CH₂–O–CH₂–C₆H₅)–C(=O)–CH₃ | 4-(9H-fluoren-9-yl)-1,4-diazepan-1-yl |
| 86 | –NH–CH(CH₂–C₆H₄–OMe)–C(=O)–CH₃ | 4-(9H-fluoren-9-yl)-1,4-diazepan-1-yl |
| 87 | –NH–CH(CH₂–(2-naphthyl))–C(=O)–CH₃ | 4-(9H-fluoren-9-yl)piperazin-1-yl |

TABLE 4-continued
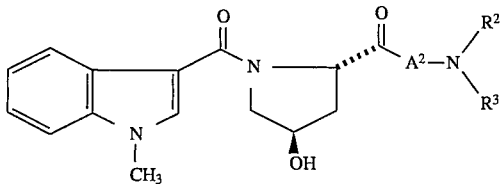
| No. | A² | -N(R²)(R³) |
|-----|----|----|
| 88 | 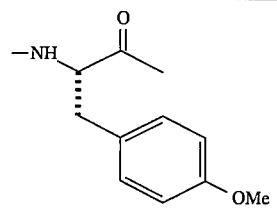 |  |
| 89 | 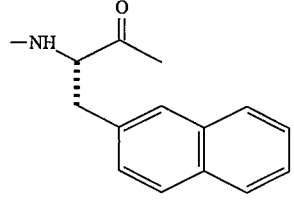 | 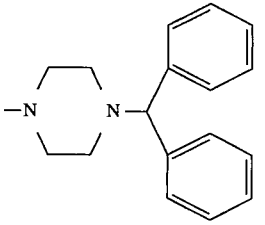 |
| 90 | 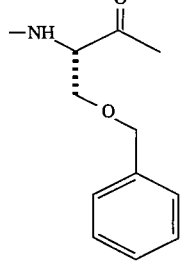 | 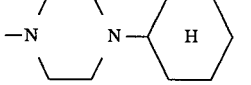 |
| 91 | 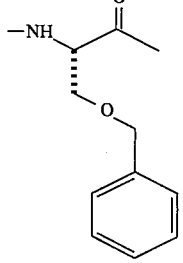 | 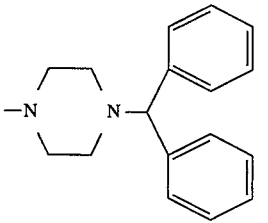 |
| 92 | 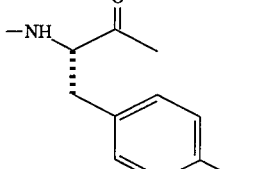 | 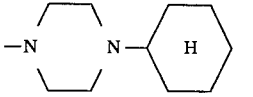 |

TABLE 4-continued
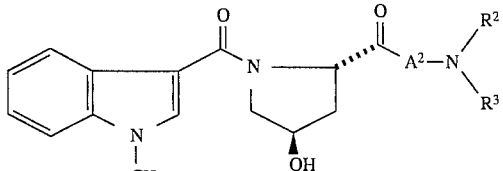
| No. | A² | —N(R²)(R³) |
|---|---|---|
| 93 | 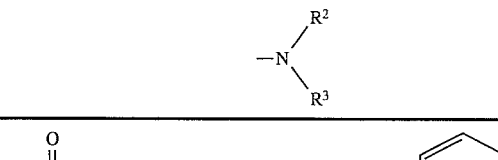 |  |
| 94 | 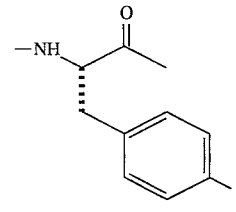 | 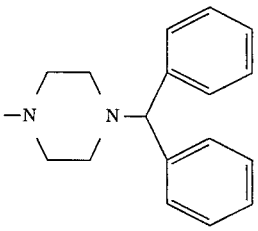 |
| 95 | 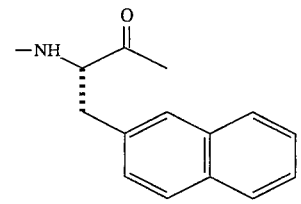 | 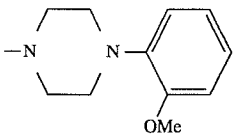 |
| 96 | 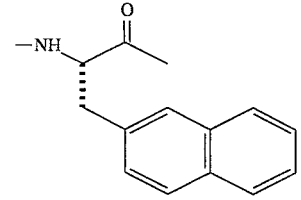 | 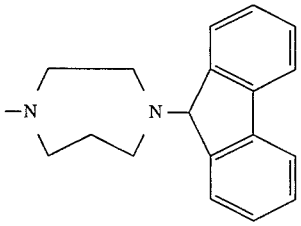 |
| 97 | 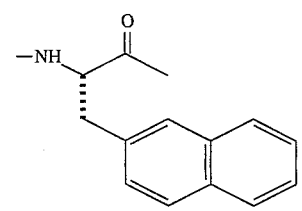 | 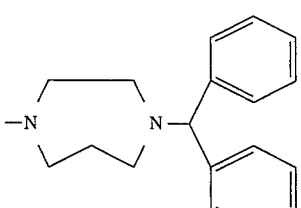 |

TABLE 4-continued
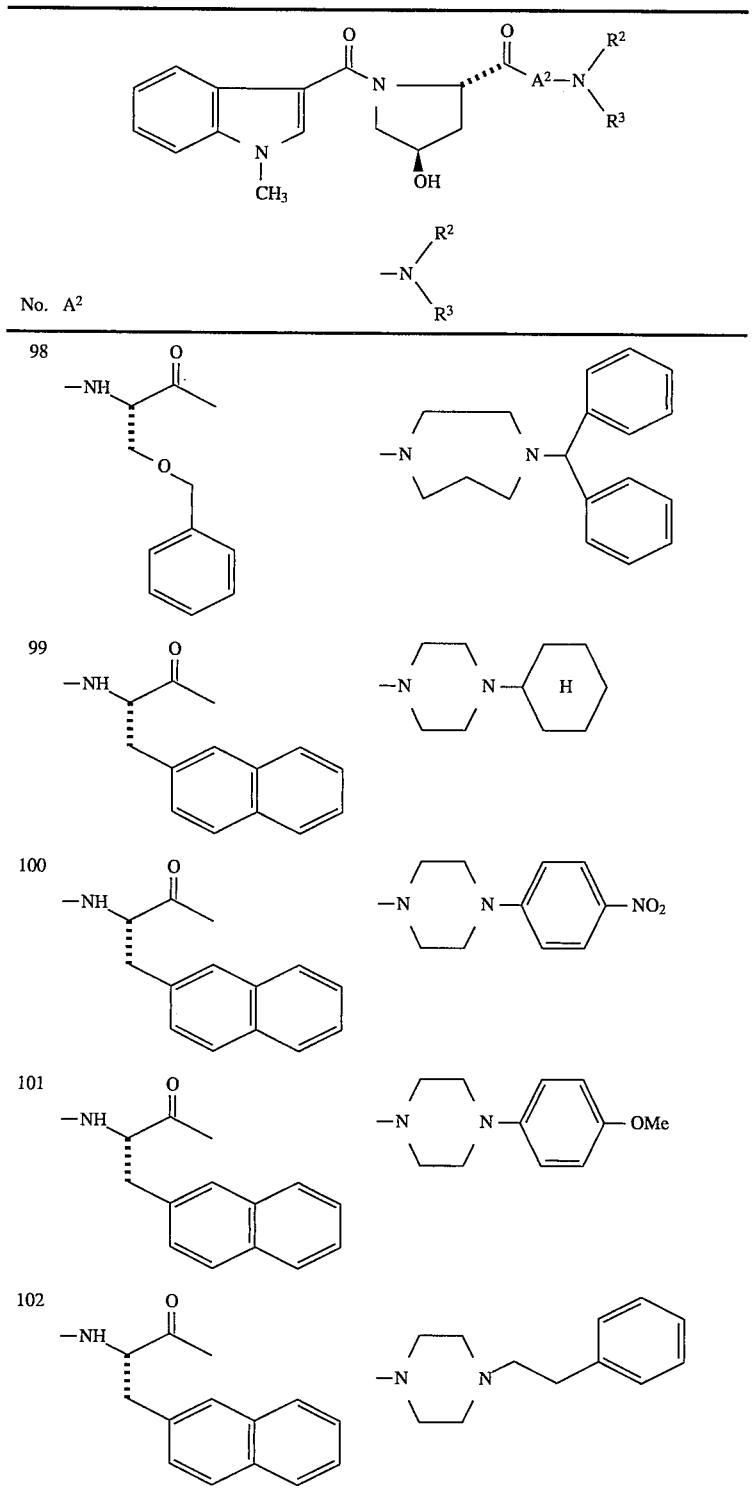

TABLE 4-continued

| No. | A² | –N(R²)(R³) |
|-----|-----|-----|
| 103 | –NH–CH(CH₂-C₆H₄-4-OMe)–C(=O)– | 4-[bis(4-fluorophenyl)methyl]piperazin-1-yl |
| 104 | –NH–CH(CH₂-(2-naphthyl))–C(=O)– | 4-[bis(4-fluorophenyl)methyl]piperazin-1-yl |
| 105 | –NH–CH(CH₂-(2-naphthyl))–C(=O)– | 4-(10,11-dihydro-5H-dibenzo[a,d]cyclohepten-5-yl)piperazin-1-yl |
| 106 | –NH–CH(CH₂-(2-naphthyl))–C(=O)– | 4-(2-chlorophenyl)piperazin-1-yl |
| 107 | –NH–CH(CH₂-C₆H₄-4-OMe)–C(=O)– | 4-phenylpiperazin-1-yl |

TABLE 4-continued
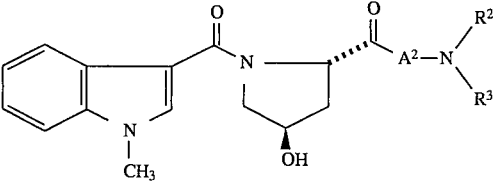
| No. | A² | —N(R²)(R³) |
|---|---|---|
| 108 | —NH—CH(CH₂-2-naphthyl)—C(O)— | 4-phenylpiperazin-1-yl |
| 109 | —NH—CH(CH₂-2-naphthyl)—C(O)— | 4-(4-methylphenyl)piperazin-1-yl |
| 110 | —NH—CH(CH₂-(4-methoxyphenyl))—C(O)— | 4-(2-cyanophenyl)piperazin-1-yl |
| 111 | —NH—CH(CH₂-2-naphthyl)—C(O)— | 4-(3,5-dimethoxyphenyl)piperazin-1-yl |
| 112 | —NH—CH(CH₂-2-naphthyl)—C(O)— | 4-[(N-methyl-N-phenylcarbamoyl)methyl]piperazin-1-yl |
| 113 | —NH—CH(CH₂-2-naphthyl)—C(O)— | 4-(2-chlorophenyl)piperazin-1-yl |

TABLE 4-continued

| No. | A² | –N(R²)(R³) |
|-----|-----|-----|
| 114 | –NH–CH(CH₂-2-naphthyl)–C(O)– | 4-(2-pyridyl)piperazin-1-yl |
| 115 | –NH–CH(CH₂-2-naphthyl)–C(O)– | 4-(2,6-dimethylphenyl)piperazin-1-yl |
| 116 | –NH–CH(CH₂-2-naphthyl)–C(O)– | 4-(2-ethoxyphenyl)piperazin-1-yl |
| 117 | –NH–CH(CH₂-4-methoxyphenyl)–C(O)– | 4-(2-ethoxyphenyl)piperazin-1-yl |
| 118 | –NH–CH(CH₂-4-methoxyphenyl)–C(O)– | 4-(2-pyridyl)piperazin-1-yl |
| 119 | –NH–CH(CH₂-2-naphthyl)–C(O)– | 4-(4-hydroxyphenyl)piperazin-1-yl |

TABLE 4-continued
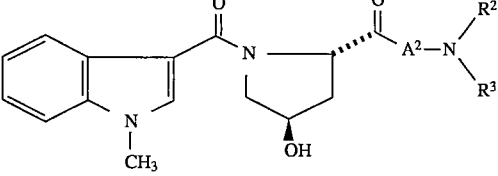
| No. | A² | −N(R²)(R³) |
|---|---|---|
| 120 | 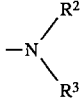 | 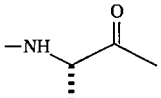 |
| 121 | 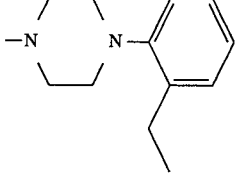 | 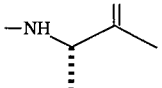 |
| 122 | 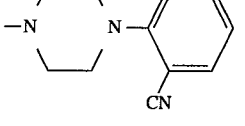 | 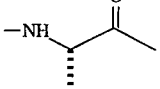 |
| 123 | 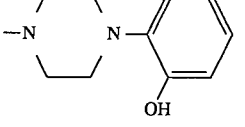 | 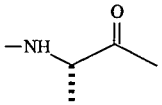 |
| 124 | 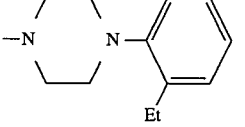 | 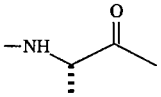 |
| 125 | 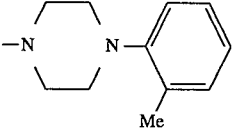 | 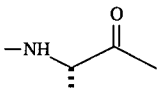 |

TABLE 4-continued

Structure: indole-N-CH3 with C(=O)-N-pyrrolidine(OH)-C(=O)-A²-N(R²)(R³)

−N(R²)(R³)

| No. | A² | −NR²R³ |
|-----|-----|--------|
| 126 | −NH−CH(CH₂−C₆H₄−OCH₃(p))−C(=O)− | −N(piperazine)−(2-Me-C₆H₄) |
| 127 | −NH−CH(CH₂−2-naphthyl)−C(=O)− | −N(piperazine)−(2-NO₂-C₆H₄) |
| 128 | −NH−CH(CH₂−2-naphthyl)−C(=O)− | −N(piperazine)−(2-F-C₆H₄) |
| 129 | −NH−CH(CH₂−2-naphthyl)−C(=O)− | −N(piperazine)−(2,4-di-OCH₃-C₆H₃) |
| 130 | −NH−CH(CH₂−2-naphthyl)−C(=O)− | −N(piperazine)−(3-OCH₃-C₆H₄) |
| 131 | −NH−CH(CH₂−2-naphthyl)−C(=O)− | −N(piperazine)−(3-CH₃-C₆H₄) |

TABLE 4-continued

| No. | A² | -N(R²)(R³) |
|---|---|---|
| 132 | -NH-CH(C(=O)CH₃)-CH₂-(1H-indol-3-yl) | -N(piperazinyl)-N-(2,5-dimethoxyphenyl) |
| 133 | -NH-CH(C(=O)CH₃)-CH₂-(1H-indol-3-yl) | -N(piperazinyl)-N-(2-chlorophenyl) |
| 134 | -NH-CH(C(=O)CH₃)-CH₂-(naphthalen-2-yl) | -N(piperazinyl)-N-(2-methylthiophenyl) |

PHYSICAL DATA

Example 1

M.p.: 112°–116° C.; $[\alpha]_D^{20}$ (MeOH)=–124.4°.

Example 2

M.p.: 70°–80° C.; $[\alpha]_D^{20}$ (MeOH)=–106.4°.

Example 3

M.p.: 98° C.; $[\alpha]_D^{20}$ (MeOH)=–137.9°.

Example 4

M.p.: 115° C.; $[\alpha]_D^{20}$ (MeOH)=–120.0°.

Example 5

M.p.: 104°–113° C.; $[\alpha]_D^{20}$ (MeOH)=–143.4°.

Example 6

M.p.: 96°–102° C.; $[\alpha]_D^{20}$ (MeOH)=–113.0°.

Example 7

M.p.: 100°–106° C.; $[\alpha]_D^{20}$ (MeOH)=–130.8°.

Example 8

M.p.: 122°–128° C.; $[\alpha]_D^{20}$ (MeOH)=–98.0°.

Example 10

M.p.: 95°–103° C.; $[\alpha]_D^{20}$ (MeOH) =–110.2°.

Example 12

M.p.: 101°–109° C.; $[\alpha]_D^{20}$ (MeOH)=–117.8°.

Example 14

M.p.: 153°–159° C.; $[\alpha]_D^{20}$ (MeOH)=–74.4°.

Example 15

M.p.: 102°–111° C.; $[\alpha]_D^{20}$ (MeOH)=–19.6°.

Example 20

M.p.: 91°–103° C.; $[\alpha]_D^{20}$ (MeOH)=–120.6°.

Example 22

M.p.: 92°–109° C.; $[\alpha]_D^{20}$ (MeOH)=−79.4°.

Example 23

M.p.: 73°–83° C.; $[\alpha]_D^{20}$ (MeOH)=−95.8°.

Example 24

M.p.: 156°–165° C.; $[\alpha]_D^{20}$ (MeOH)=−52.8°.

Example 28

M.p.: 171°–186° C.; $[\alpha]_D^{20}$ (MeOH)=−121.6°.

Example 30

M.p.: 75°–85° C.; $[\alpha]_D^{20}$ (MeOH)=−111.3°.

Example 31

M.p.: 80°–90° C.; $[\alpha]_D^{20}$ (MeOH)=−111.7°.

Example 32

M.p.: 75°–85° C.; $[\alpha]_D^{20}$ (MeOH)=−93.8°.

Example 33

M.p.: 105°–115° C.; $[\alpha]_D^{20}$ (MeOH)=−88.7°.

Example 34

M.p.: 75°–85° C.; $[\alpha]_D^{20}$ (MeOH)=−65.8°.

Example 35

M.p.: 45°–55° C.; $[\alpha]_D^{20}$ (MeOH)=−107.0°.

Example 36

M.p.: 45°–55° C.; $[\alpha]_D^{20}$ (MeOH)=−94.3°.

Example 37

M.p.: 85°–95° C.; $[\alpha]_D^{20}$ (MeOH)=−75.9°.

Example 38

M.p.: 90°–97° C.; $[\alpha]_D^{20}$ (MeOH)=−137.5°.

Example 39

M.p.: 80°–95° C.; $[\alpha]_D^{20}$ (MeOH)=−98.0°.

Example 40

M.p.: 97°–105° C.; $[\alpha]_D^{20}$ (MeOH)=−66.9°.

Example 41

M.p.: 100°–112° C.; $[\alpha]_D^{20}$ (MeOH)=−88.6°.

Example 42

M.p.: 105°–110° C.; $[\alpha]_D^{20}$ (MeOH)=−94.4°.

Example 43

M.p.: 107°–115° C.; $[\alpha]_D^{20}$ (MeOH)=−108.1°.

Example 44

M.p.: 208°–217° C.; $[\alpha]_D^{20}$ (MeOH:THF=2:1)=−72.8°.

Example 45

M.p.: approx. 85°(D.); $[\alpha]_D^{20}$ (MeOH)=−84.8°.

Example 48

M.p.: 104°–111° C. (decomp.); $[\alpha]_D^{20}$ (MeOH)=−103.1°.

Example 49

M.p.: 118°–123° C.; $[\alpha]_D^{20}$ (MeOH)=−66.0°.

Example 51

M.p.: 123°–128° C.; $[\alpha]_D^{20}$ (MeOH)=−111.0°.

Example 55

M.p.: 60°–78° C.; $[\alpha]_D^{20}$ (MeOH)=−103.7°.

Example 57

M.p.: 61°–64° C.; $[\alpha]_D^{20}$ (MeOH)=−107.6°.

Example 58

M.p.: 55°–65° C.; $[\alpha]_D^{20}$ (MeOH)=−76.1°.

Example 59

M.p.: 85°–89° C.; $[\alpha]_D^{20}$ (MeOH)=−118.6°.

Example 60

M.p.: 45°–56° C.; $[\alpha]_D^{20}$ (MeOH)=−78.1°.

Example 61

M.p.: 68°–72° C.; $[\alpha]_D^{20}$ (MeOH)=−108.2°.

Example 62

M.p.: 56°–60° C.; $[\alpha]_D^{20}$ (MeOH)=−47.0°.

Example 68

M.p.: −(glassy); $[\alpha]_D^{20}$ (MeOH)=−58.1°.

Example 70

M.p.: 66°–76° C.; $[\alpha]_D^{20}$ (MeOH)=−37.6°.

Example 71

M.p.: −(pasty); $[\alpha]_D^{20}$ (MeOH)=−50.2°.

Example 73

FAB-MS: $(M+H)^+$ 640.2

Example 74

M.p.: 93°–95° C.; FAB-MS: $(M+H)^+$ 638.4

Example 75

M.p.: 67°–70° C.; FAB-MS: $(M+H)^+$ 640.4

Example 76

M.p.: over 200° C.; FAB-MS: $(M+H)^+$ 638.3

Example 77

M.p.: 133°–138° C.; FAB-MS: $(M+H)^+$ 698.4

Example 78
M.p.: over 200° C.; FAB-MS: (M+H)⁺640.3

Example 79
M.p.: 109°–114° C.; FAB-MS: (M+H)⁺668.4

Example 80
M.p.: 142°–146° C.; FAB-MS: (M+H)⁺668.4

Example 81
M.p.: 109°–115° C.; FAB-MS: (M+H)⁺640.5

Example 82
M.p.: 145°–152° C. foam; FAB-MS: (M+H)⁺655.3

Example 83
M.p.: 110°–115° C.; FAB-MS: (M+H)⁺655.3

Example 84
M.p.: 144°–150° C.; FAB-MS: (M+H)⁺698.4

Example 85
M.p.: 115°–122° C.; FAB-MS: (M+H)⁺712.4

Example 86
M.p.: 132°–140° C.; FAB-MS: (M+H)⁺712.4

Example 87
M.p.: 144°–149° C.; FAB-MS: (M+H)⁺718.4

Example 88
FAB-MS: (M+H)⁺714.4

Example 89
M.p.: 140°–144° C.; FAB-MS: (M+H)⁺720.3

Example 91
M.p.: 110°–117° C.; FAB-MS: (M+H)⁺700.4

Example 92
M.p.: 101°–108° C.; FAB-MS: (M+H)⁺616.5

Example 93
M.p.: 138°–143° C.; FAB-MS: (M+H)⁺700.4

Example 94
M.p. Base: 126°–134° C.; FAB-MS: (M+H)⁺660.3 HU salt 174°–178° C.

Example 95
M.p.: 143°–148° C.; FAB-MS: (M+H)⁺732.3

Example 96
M.p.: 135°–142° C. foams; FAB-MS: (M+H)⁺734.3

Example 97
M.p.: 140°–144° C.; FAB-MS: (M+H)⁺688.3

Example 98
FAB-MS: (M+H)⁺714.3

Example 99
FAB-MS: (M+H)⁺636.3

Example 100
M.p.: 143°–150° C.; FAB-MS: (M+H)⁺675.2

Example 101
M.p.: 122°–128° C.; FAB-MS: (M+H)⁺660.1

Example 102
FAB-MS: (M+H)⁺658.5

Example 103
FAB-MS: (M+H )⁺736.3

Example 104
FAB-MS: (M+H)⁺756.3

Example 105
M.p.: 142°–148° C. foams; FAB-MS: (M+H)⁺746.6

Example 106
M.p.: 137°–145° C.;

Example 107
M.p.: 124°–133° C.; FAB-MS: (M+H)⁺610.5

Example 108
M.p.: 156°–159° C.; FAB-MS: (M+H)⁺630.5

Example 109
M.p.: 206°–211° C.;

Example 110
FAB-MS: (M+H)⁺635.3

Example 111
M.p.: 125°–128° C. foams; FAB-MS: (M+H)⁺690.5

Example 112
M.p.: 138°–140° C. foams; FAB-MS: (M+H)⁺701.5

Example 113
M.p.: 201°–203° C.;

Example 114
M.p.: 144°–147° C.; FAB-MS: (M+H)⁺631.3

Example 115
M.p.: 134°–139° C.; FAB-MS: (M+H)⁺658.3

Example 116
M.p.: 130°–133° C.; FAB-MS: (M+H)⁺674.5

Example 117
M.p.: 110°–115° C.; FAB-MS: (M+H)⁺654.5

Example 118
M.p.: 107°–112° C. foams; FAB-MS: (M+H)⁺611.4

Example 119
M.p.: 159°–162° C.; FAB-MS: (M+H)⁺646.3

Example 120
M.p.: 117°–122° C.; FAB-MS: (M+H)⁺638.3

Example 122
M.p.: 148°–152° C.; FAB-MS: (M+H)⁺646.3

Example 123
M.p.: 128°–132° C.; FAB-MS: (M+H)⁺658.4

Example 124
FAB-MS: (M+H)⁺644.5

Example 125
FAB-MS: (M+H)⁺674

Example 126
FAB-MS: (M+H)⁺623.4

TABLE 5

Examples 135–157

| Example 135 | 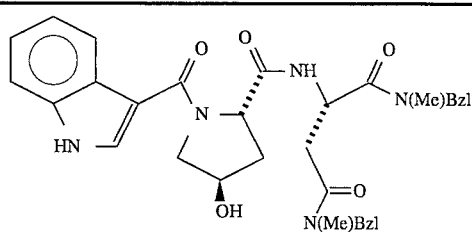 | Mp.: 80–88° C.<br>$[\alpha]_D^{20}$ (MeOH) = −134.4° |
|---|---|---|
| Example 136 | 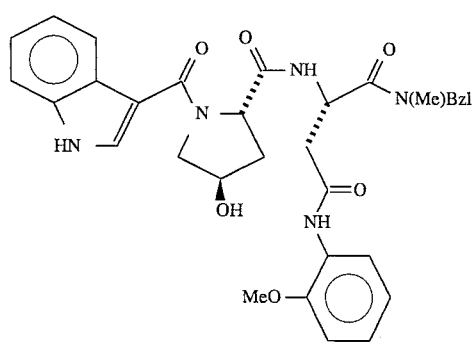 | Mp.: 128–136° C.<br>$[\alpha]_D^{20}$ (MeOH) = −137.5° |
| Example 137 | 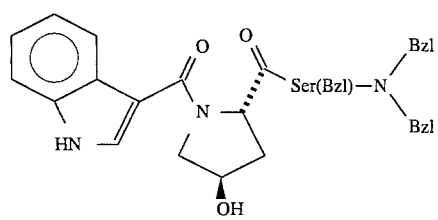 | Mp.: 85–95° C.<br>$[\alpha]_D^{20}$ (MeOH) = −79.6° |
| Example 138 | 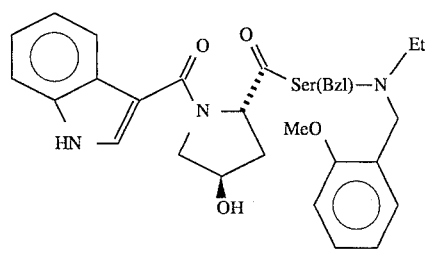 | Mp.: 77–82° C.<br>$[\alpha]_D^{20}$ (MeOH) = −103.4° |

TABLE 5-continued
Examples 135–157
Example 139 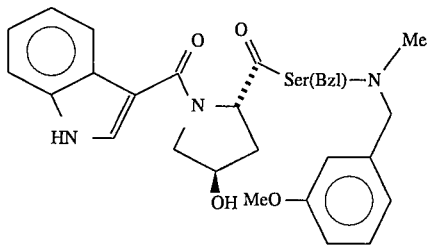 Mp.: 78–84° C.
$[\alpha]_D^{20}$ (MeOH) = –97.0°
Example 140 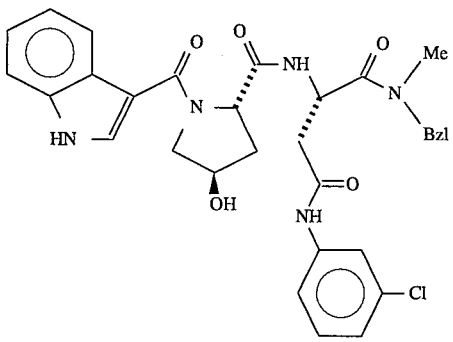 Mp.: 215–228° C. (dec.)
Example 141 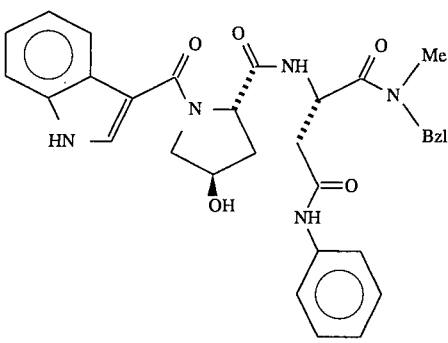 Mp.: 120–140° C.
$[\alpha]_D^{20}$ (MeOH) = –142.1°
Example 142 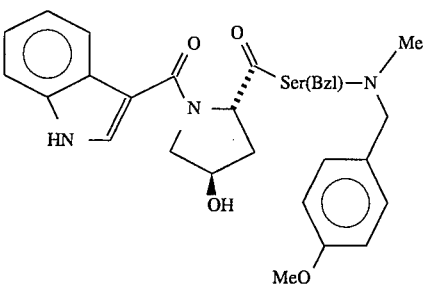 Mp.: 80–87° C.
$[\alpha]_D^{20}$ (MeOH) = –95.2°
Example 143 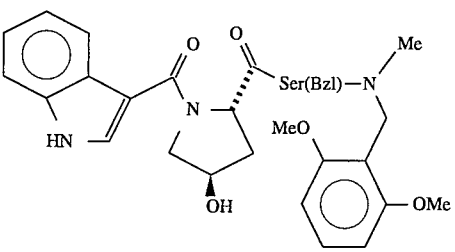 Mp.: 84–88° C.
$[\alpha]_D^{20}$ (MeOH) = –113.0°

TABLE 5-continued
Examples 135–157
| | | |
|---|---|---|
| Example 144 | 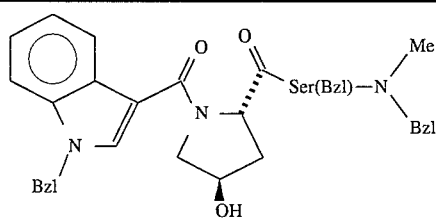 | Mp.: approx. 80° C. (dec.)<br>$[\alpha]_D^{20}$ (MeOH) = −82.4° |
| Example 145 | 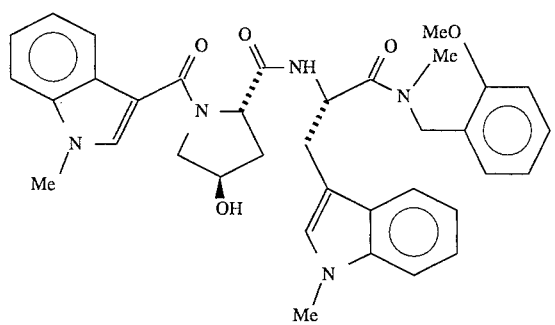 | Mp.: 127–133° C. (dec.)<br>$[\alpha]_D^{20}$ (MeOH) = −105.8° |
| Example 146 | 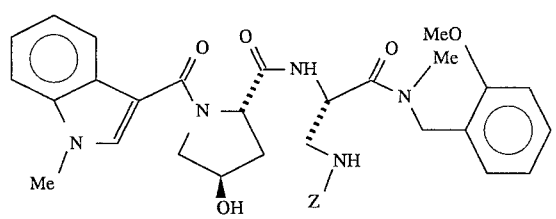 | Mp.: 95–100° C.<br>$[\alpha]_D^{20}$ (MeOH) = −111.5°. |
| Example 147 | 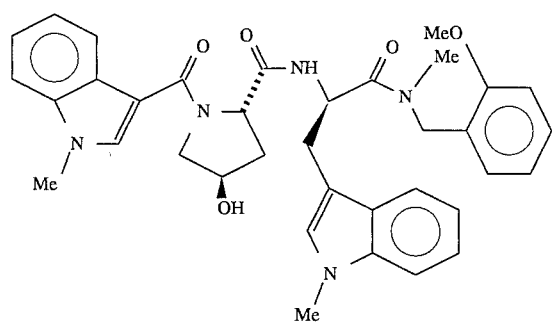 | Mp.: 112–122° C. (dec.)<br>$[\alpha]_D^{20}$ (MeOH) = −65.8°. |
| Example 148 | 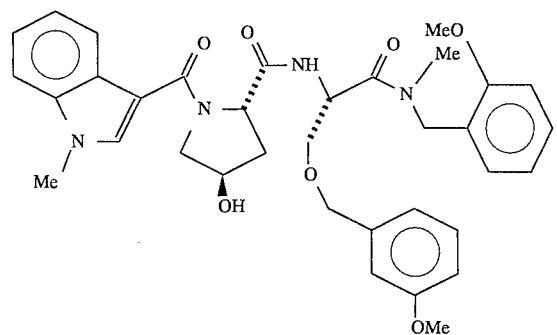 | Mp.: approx. 80° C. (dec.)<br>$[\alpha]_D^{20}$ (MeOH) = −85.3°. |

TABLE 5-continued
Examples 135–157
Example 149 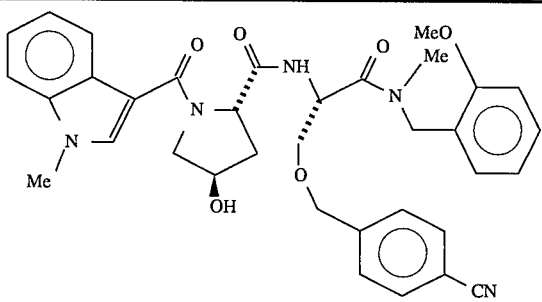 Mp.: approx. 85° C. (dec.)
$[\alpha]_D^{20}$ (MeOH) = $-90.6°$.
Example 150 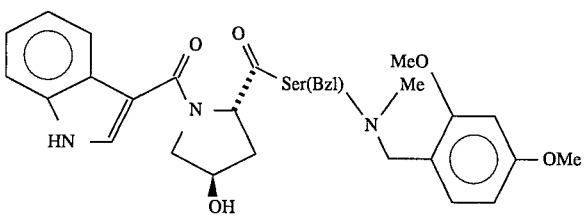 Mp.: 91–98° C.
$[\alpha]_D^{20}$ (MeOH) = $-112.4°$
Example 151 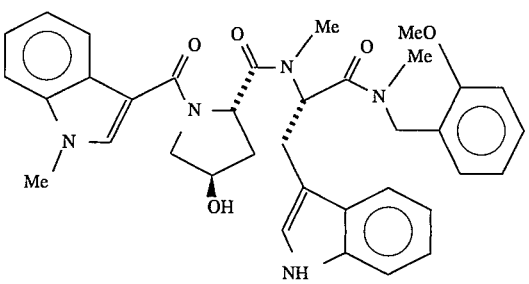 Mp.: approx. 124° C. (dec.)
$[\alpha]_D^{20}$ (MeOH) = $-151.5°$
Example 152 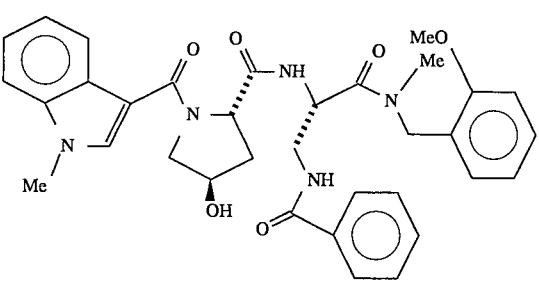 Mp.: 215–217° C.
$[\alpha]_D^{20}$ (DMSO) = $-121.8°$
Example 153 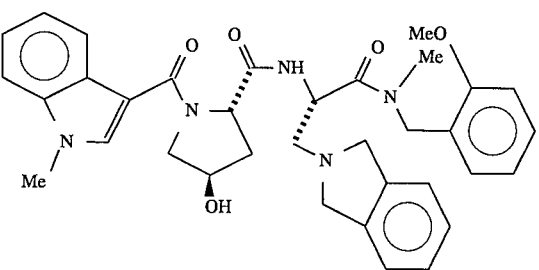 Mp.: 110–115° C.
$[\alpha]_D^{20}$ (MeOH) = $-94°$ TABLE 5-continued
Examples 135–157
| Example 154 | 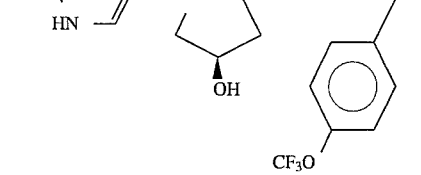 | Mp.: 83–91° C.<br>$[\alpha]_D^{20}$ (MeOH) = −88.4° |
| Example 155 | 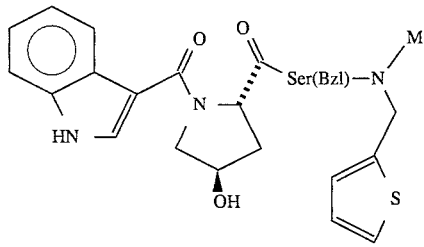 | Mp.: 87–93° C.<br>$[\alpha]_D^{20}$ (MeOH) = −105.4° |
| Example 156 | 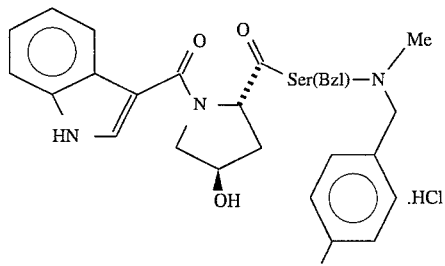 | Mp.: 117–127° C.<br>$[\alpha]_D^{20}$ (MeOH) = −84.2° |
| Example 157 | 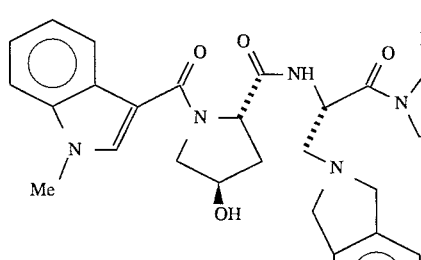 | Mp.: 128–130° C.<br>$[\alpha]_D^{20}$ (MeOH) = −94.8° |

TABLE 6
Examples 158–182
Example 158
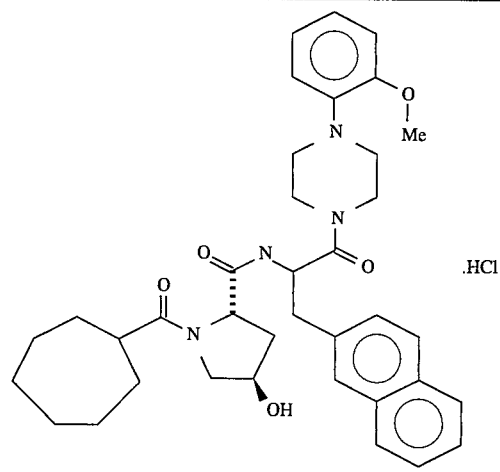
Example 159
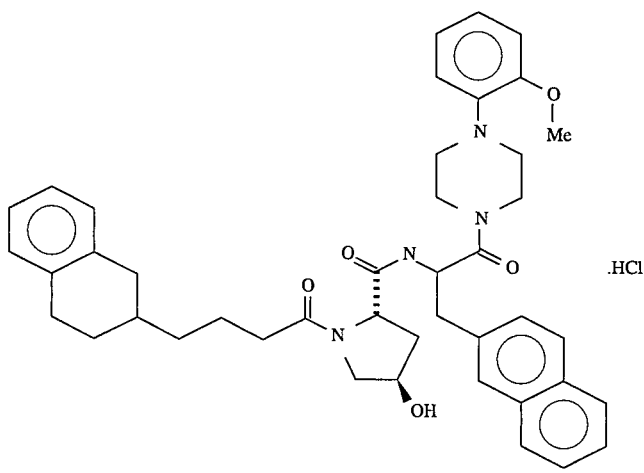
Example 160
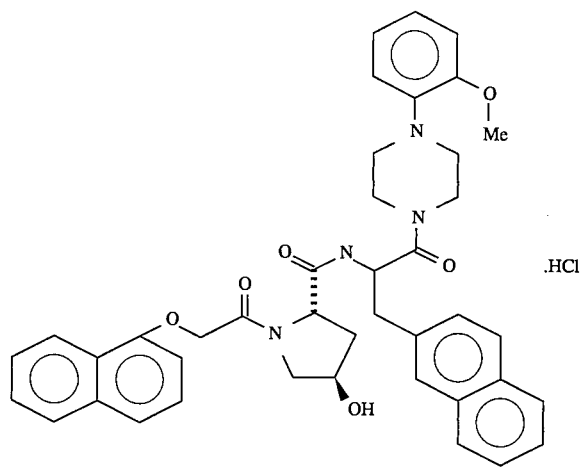

TABLE 6-continued
Examples 158–182
Example 161
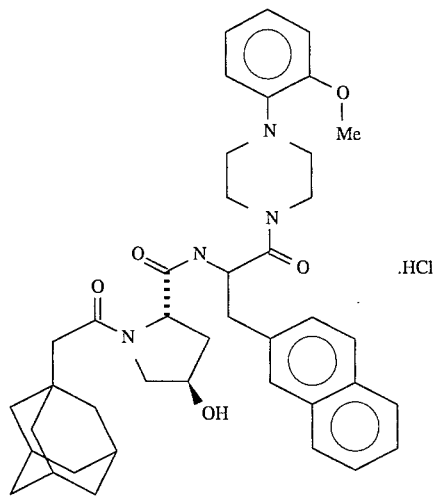
Example 162
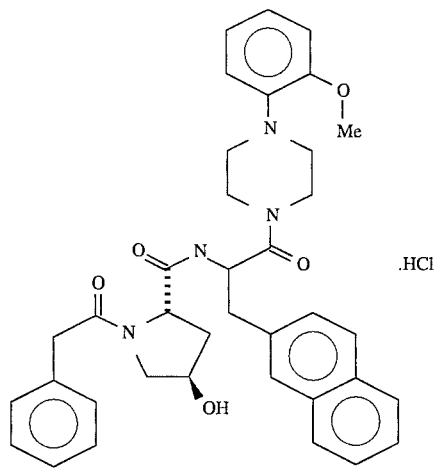
Example 163
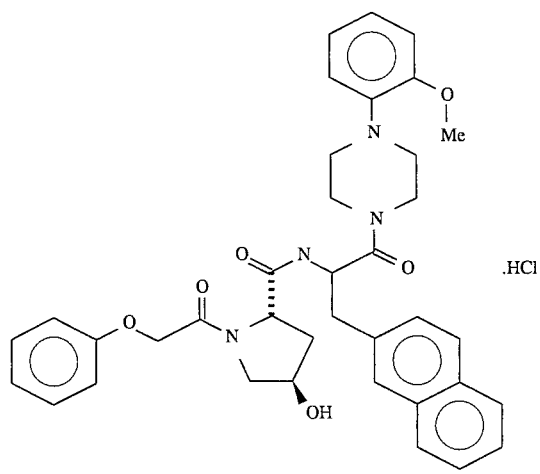

TABLE 6-continued
Examples 158–182
Example 164
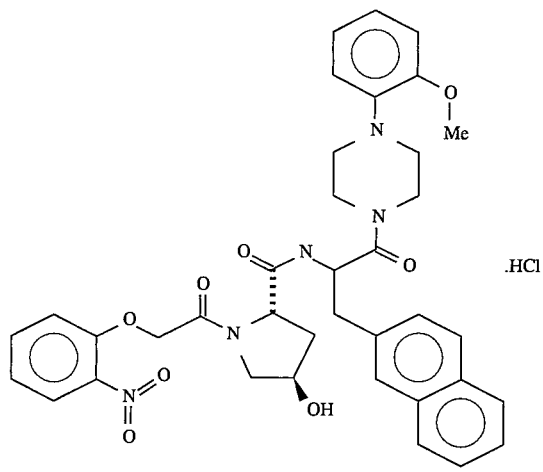
Example 165
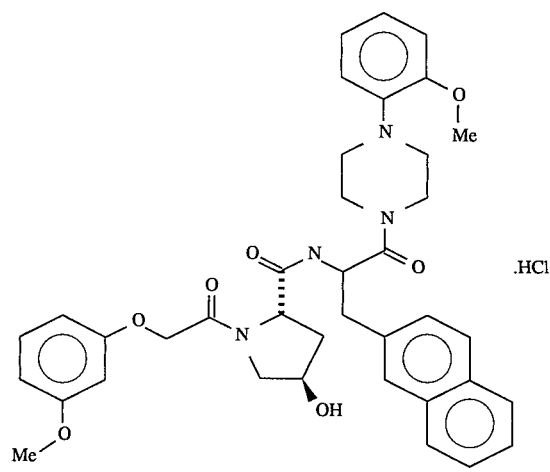
Example 166
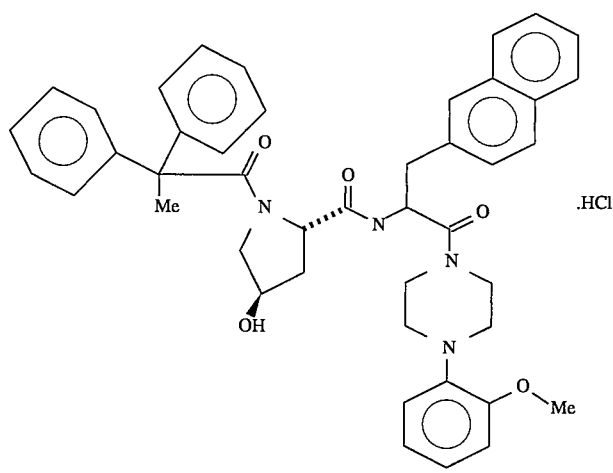

TABLE 6-continued
Examples 158–182
Example 167
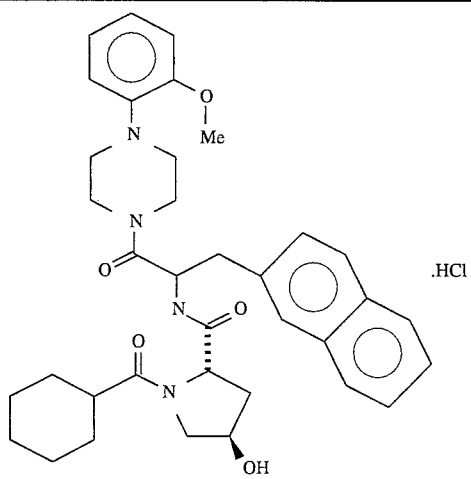
.HCl
Example 168
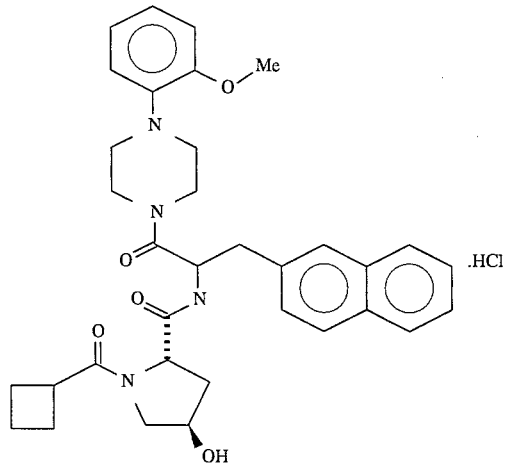
.HCl
Example 169
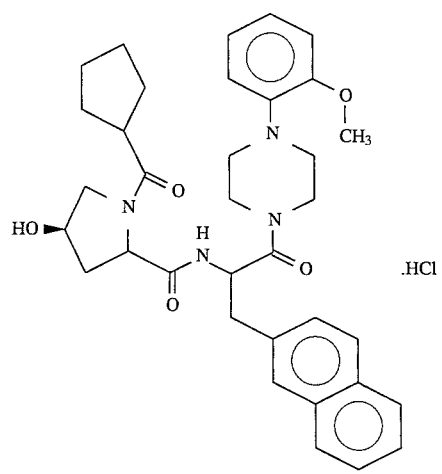
.HCl TABLE 6-continued
Examples 158–182
Example 170
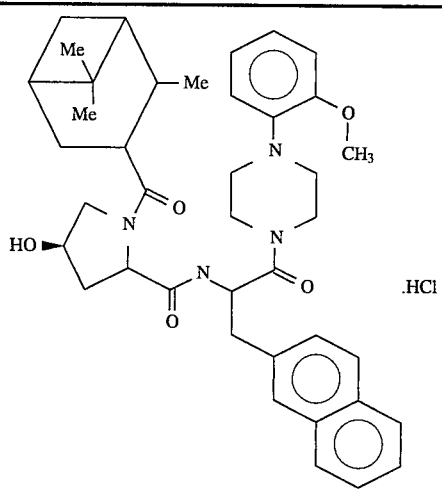
.HCl
Example 171
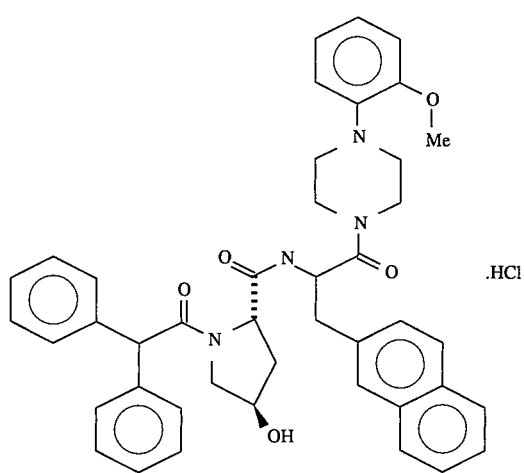
.HCl
Example 172
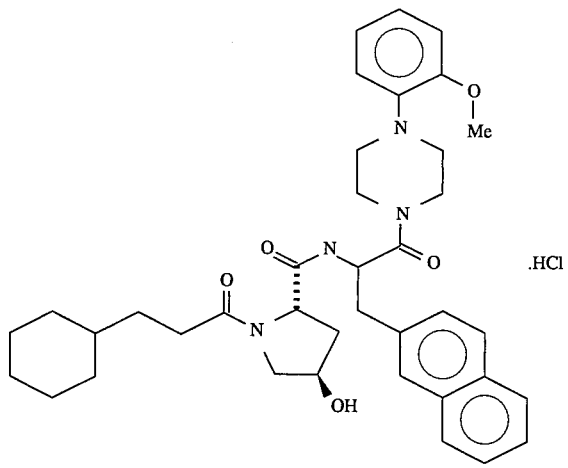
.HCl

TABLE 6-continued
Examples 158–182
Example 173
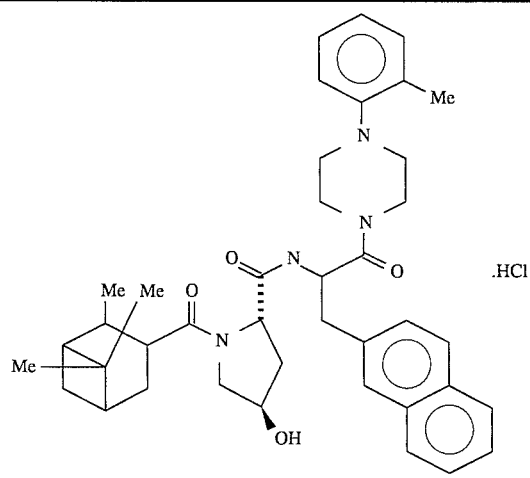
Example 174
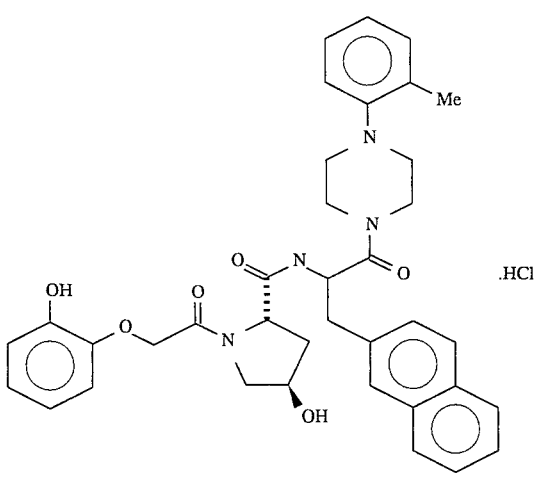
Example 175
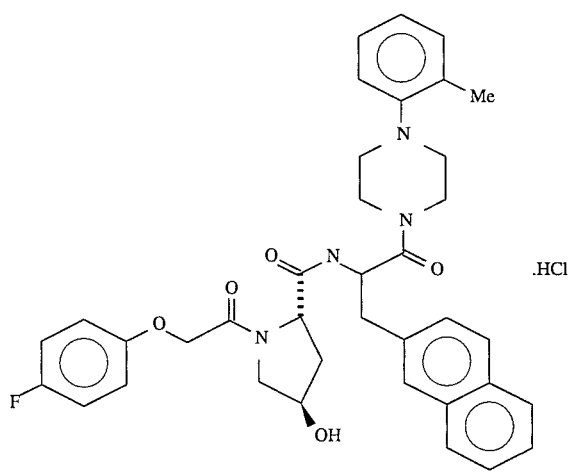

TABLE 6-continued
Examples 158–182
Example 176
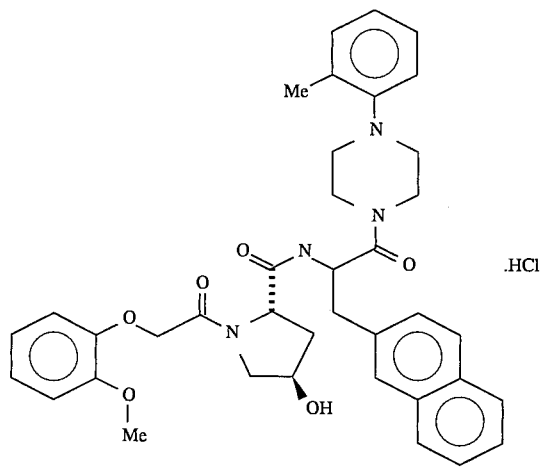
Example 177
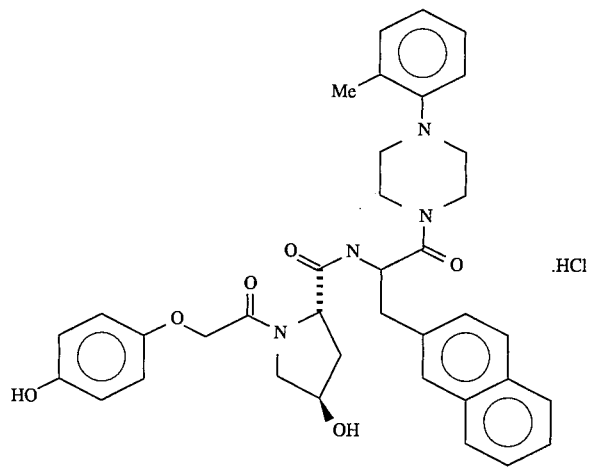
Example 178
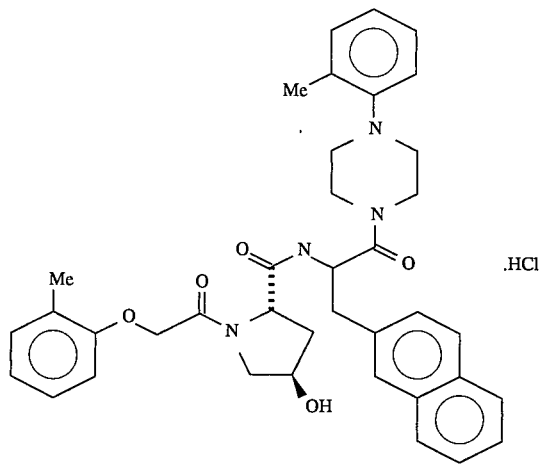

TABLE 6-continued
Examples 158–182
Example 179
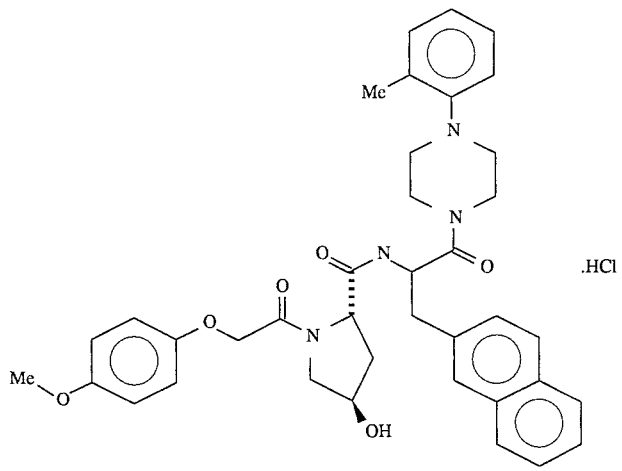
Example 180
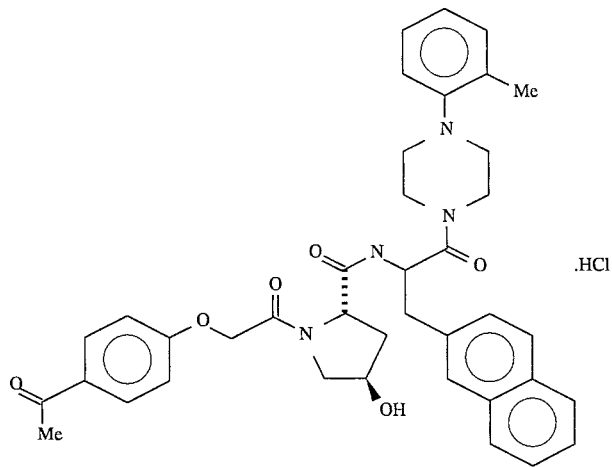
Example 181
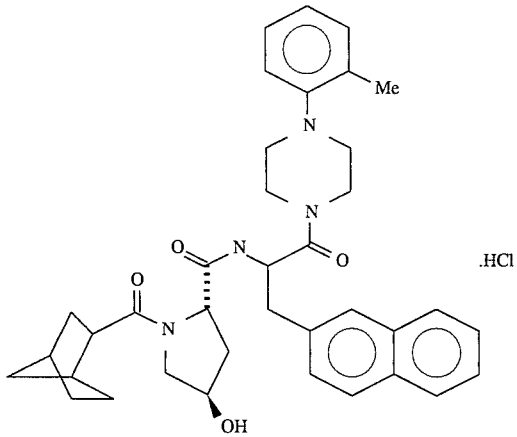

TABLE 6-continued
Examples 158–182
Example 182
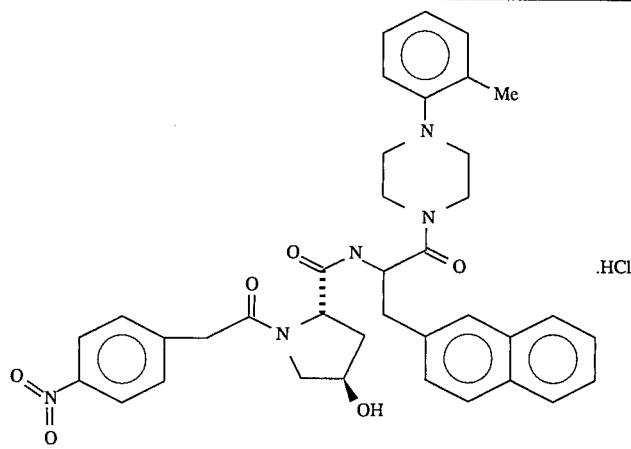
| Example No. | Physical data<br>FAB MS: (M + H)⁺ |
|---|---|
| 158 | 627.4 |
| 159 | 703.5 |
| 160 | 687.4 |
| 161 | 679.5 |
| 162 | 621.3 |
| 163 | 637.3 |
| 164 | 682.3 |
| 165 | 667.2 |
| 166 | 711.3 |
| 167 | 613.3 |
| 168 | 585.2 |
| 169 | 599.4 |
| 170 | 667.3 |
| 171 | 697.4 |
-continued
| Example No. | Physical data<br>FAB MS: (M + H)⁺ |
|---|---|
| 172 | 641.4 |
| 173 | 651.5 |
| 174 | 637.3 |
| 175 | 639.3 |
| 176 | 651 |
| 177 | 637 |
| 178 | 635 |
| 179 | 651 |
| 180 | 663.1 |
| 181 | 608.4 |
| 182 | 650.3 |
Example 201
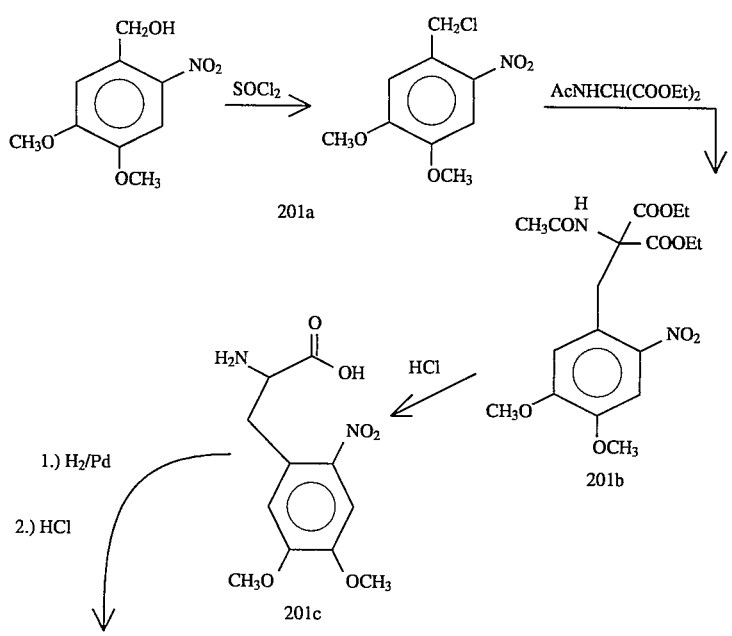

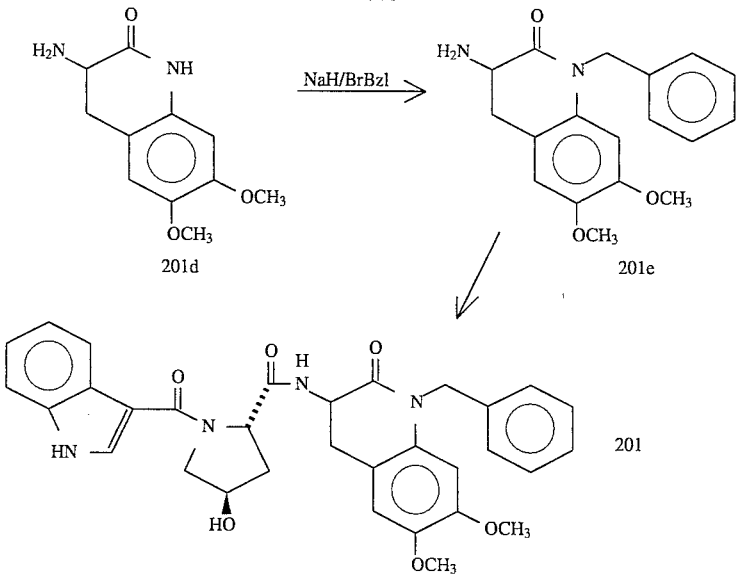

Preparation of 201a 10.7 g of 6-nitroveratrylalcohol are suspended in 20 ml of absolute $SOCl_2$ and 2.7 ml of absolute pyridine, heated to boiling point and for half an hour a mixture of 4 ml of thionylchloride and 2 ml of $CH_2Cl_2$ is added dropwise. Then it is boiled for 1 hour under reflux, cooled down and the reaction mixture is stirred into a mixture of 20 g of ice and 20 g of water. The organic phase is thoroughly washed with water and $NaHCO_3$ solution, dried with a $Na_2SO_4$ and concentrated on the rotary evaporator. 11.4 g of 201a are obtained as dark brown oil (yield 98%).

Preparation of 201b

As described in J. Med. Chem. 9, 828 (1966), 11.2 g of 201a are reacted with 10.5 g of acetamidomalonic acid diethylester whereby 16.2 g of 201b are obtained in the form of yellow crystals (yield 81%). M.p.: 176°–178° C.

Preparation of 201c

According to instructions of A. L. Davis (J. Med. Chem. 9, 828, (1966) 16 g of 201b are hydrolysed with 120 ml of concentrated hydrochloric acid reducing initially 210c.HCl. This was converted by means of ammonium into free amino acid 201c resulting in 7.4 g in the form of greenish crystals (yield 71%). M.p.: about 207° C. (decomp.).

Preparation of 201d

As described by A. L. Davis et al. (J. Med. Chem. 9, 828 (1966)), 5.4 g of 201c are hydrogenated by means of 0.6 g of Pd-Mohr. The resultant amino compound is boiled on the reflux together with 68 ml of ethanol and 12 ml of concentrated hydrochloric acid for half an hour whilst stirring. After cooling down, this is mixed with 26 ml of ether, suction filtered and the precipitate is washed with ice cold ethanol and ether and dried at 80° C. 3.3 g of 201d.HCl are obtained in the form of a light grey solid substance (yield 63%). M.p.: about 296° (decomp.).

Preparation of 201e 1.3 g of 201d.HCl are dissolved in 15 ml of DMF, mixed with 0.42 g of NaH-dispersion (60% in mineral oil), stirred for half an hour at ambient temperature, then 0.66 ml of benzyl bromide are slowly added dropwise and the mixture is stirred for 1 hour at ambient temperature. The reaction mixture is mixed in about 200 ml of water and extracted twice with ethyl acetate. The combined ethyl acetate phases are filtered and concentrated, taken up in ether and mixed with volatile HCl and concentrated again. The solid residue is mixed with ether, suction filtered and dried over KOH in the desiccator, whereby 1.25 g of 201e.HCl are obtained in the form of a beige solid substance (yield 72%). M.p.: 98°–116° C.

Preparation of (201)

a) Synthesis of (2S, 4R)-N-(indol-3-yl-carbonyl)-4-hydroxy-proline: 9.2 g (2S, 4R)-hydroxyproline, 105 ml $CH_2Cl_2$ and 35.4 ml chlorotrimethylsilane are united, stirred for 1 hour at ambient temperature, then boiled under refluxed for 1 hour, 39 ml triethylamine is added dropwise within 15 minutes and boiled for a further 15 minutes under reflux. The reaction mixture is cooled to –70° C. and within 40 minutes a solution of indol-3-carboxylic acid chloride is added dropwise in 100 ml of $CH_2Cl_2$ and 50 ml of ethyl acetate. The mixture is stirred for another 20 minutes at –70° C. and heated within 1½ hours to ambient temperature. Whilst cooling with ice, 190 ml of water and 25 ml of 2N hydrochloric acid are added successively, the mixture is stirred for another 45 minutes at ambient temperature and left to stand overnight at ambient temperature. The precipitate formed is suction filtered, washed successively with $CH_2Cl_2$, water, ethyl acetate and ether and dried in the desiccator. 15.5 g of (2S, 4R)-N-(indol-3-ylcarbonyl)-4-hydroxyproline is obtained in the form of beige crystals (yield 91%). $[\alpha]_D^{20}$ (MeOH)=–136.4° C.

b) Coupling of (2S, 4R)-N-(indol-3-ylcarbonyl)-4-hydroxyproline with 201e: 0.41 g of (2S, 4R)-N-(indol-3-ylcarbonyl)-4-hydroxyproline is dissolved in 150 ml of DMF, mixed with 0.81 g of 201e.HCl and adjusted to pH 8.5 with triethylamine. It is cooled down to –20° C., mixed with 0.4 ml of DPPA (diphenylphosphorylazide), left for 3 days in the freezer and for 1 day at 8° C. in the refrigerator. The reaction mixture is concentrated on the rotary evaporator, taken up in $CH_2Cl_2$ and extracted successively with diluted hydrochloric acid, saturated $NaHCO_3$ solution and 10% NaCl solution. The organic phase is filtered, concentrated and the residue is chromatographed over silica gel. 0.48 g (201) is obtained as solid substance from the uniform fractions of the eluant (yield 56%). M.p.: 128°–142° C. (decomp.). $[\alpha]_D^{20}$ (MeOH)=–103.7° C.

The substance constitutes an approximate 1:1-diastereomeric mixture wherein in the amine part $R^2$ is R- on the one hand, S-configuration on the other hand.

Example 202, (2S, 4R)S-form and Example 203, (2S, 4R)R-form

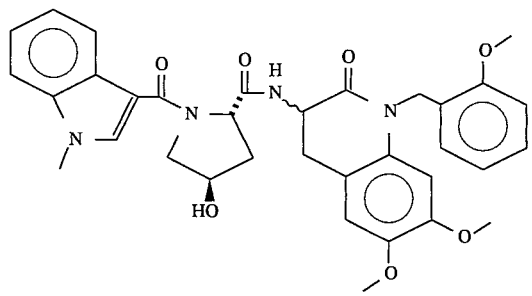

The synthesis was carried out as described in Example 201 except that 1-methyl-indol-3-carboxylic acid chloride was used instead of indol-3-carboxylic acid chloride and 2-methoxybenzylchloride instead of benzylbromide. Finally, the substance mixture of the last reaction stage was separated on a silica gel column into the diasteromers using ethyl acetate/MeOH (4:1).

The substance (202) migrating more quickly ($R_f$=0.44) could be obtained in an amount of 0.82 g (yield 26%), which is probably the (2S, 4R) S-form. M.p.: 201°–208° C. $[\alpha]_D^{20}$ (DMSO)=–135° C.

0.31 g (yield 10%) was obtained from the slower migrating substance (203) ($R_f$=0.38); this is probably the (2S, 4R) R-form. M.p.: 123°–133° C. $[\alpha]_D^{20}$ (MeOH )=–24.2° C.

Example 214

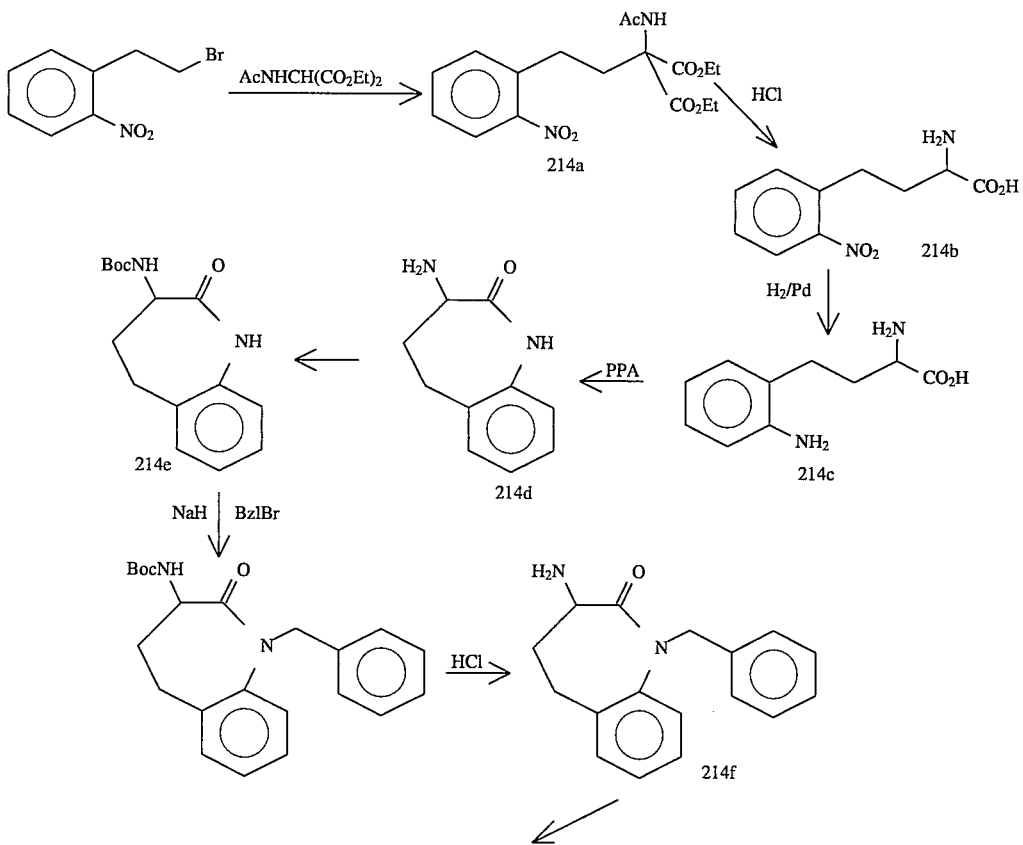

-continued

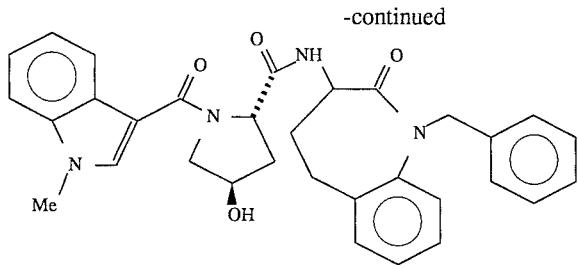

Preparation of 214a

As described for the preparation of 201b, 22.5 g of 2-(2-nitrophenyl)-ethylbromide is reacted with 23.4 g of acetamidomalonic acid diethylester, whereby 29.6 g of 214a is obtained (yield 83%).

Preparation of 214b

Analogously to the preparation of 201c, 29.6 g of 214a is hydrolysed with 315 ml of concentrated HCl, whereby 16.5 g of 214b are isolated in the form of light yellow crystals (yield 91%).

Preparation of 214c 16.2 g of 214b is hydrogenated under pressure in a solution of 600 ml of MeOH and 200 ml of water using 3.25 g of Pd-Mohr. In so doing, 12.9 g of 214c is obtained in the form of a light yellow powder (yield 92%).

Preparation of 214d 12.8 g of 214c is combined with 100 g of polyphosphoric acid and heated to 120°–130° C. for 3 hours whilst stirring. After cooling the mixture is stirred in approximately 400 g of ice, alkalised with ammonium and extracted three times with 400 ml of $CH_2Cl_2$. The organic extracts are concentrated by evaporation and the residue is mixed with ether and dried. 9.4 g of 214d are obtained in the form of beige crystals (yield 81%).

Preparation of 214e 9.4 g of 214d are dissolved in 100 ml of THF and 50 ml of water, mixed with 12.8 g of $(Boc)_2O$ and stirred for 30 minutes at ambient temperature. The THF is removed on the rotary evaporator and the resultant precipitate is suction filtered and dried. 14.5 g of 214e is obtained in the form of light beige crystals (yield 98%).

Preparation of 214 f 1.9 g of 214e is dissolved in 40 ml of DMF, mixed with 0.3 g of NaH-dispersion (60% in oil) and stirred for 45 minutes at ambient temperature. To the reaction mixture, a solution of 0.9 ml of benzylbromide in 10 ml of THF is added dropwise at ambient temperature within 10 minutes, whilst stirring, and stirred for a further 20 minutes at ambient temperature. The mixture is rotated in and the residue is mixed with 40 ml of $CH_2Cl_2$, 4 ml of anisole and 40 ml of 4NHCl in dioxane and left to stand for 1 hour at ambient temperature. The reaction mixture is concentrated by evaporation on the rotary evaporator, the residue is washed with ether and then dissolved in 50 ml of water. The solution is extracted twice with ether, the aqueous phase is alkalised with 1M of $Na_2CO_3$ solution and extracted twice with ether. As a result of filtration and concentration by evaporation 1.63 g of 214f is obtained in the form of a brownish, tough oil (yield 87%).

Preparation of 214

As described for the preparation of 201, 1.75 g of (2S, 4R)-N-(1-methyl-indol-3-ylcarbonyl)-4-hydroxyproline is coupled with 1.62 g of 214f. 2.6 g of 214 is obtained in the form of white crystals (yield 80%). M.p.: 118°–123° C.

TABLE 7

Summary of the Examples which may be prepared analogously.

Example 201

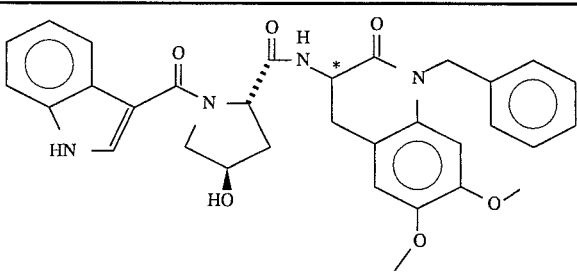

*R/S

TABLE 7-continued
Summary of the Examples which may be prepared analogously.
Example 202
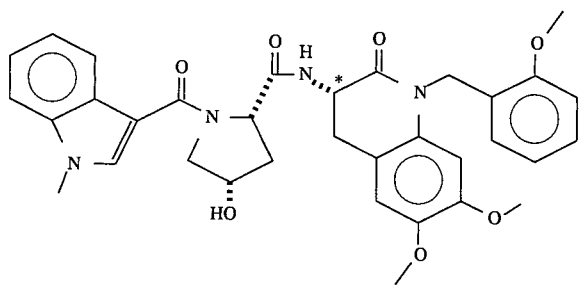
*S
Example 203
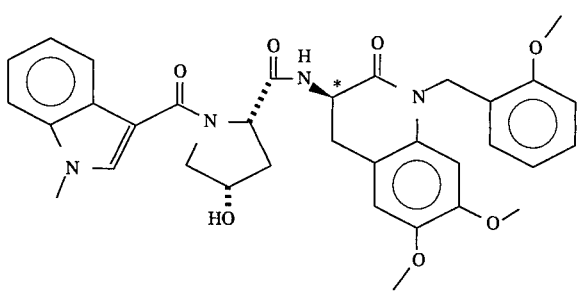
*R
Example 204
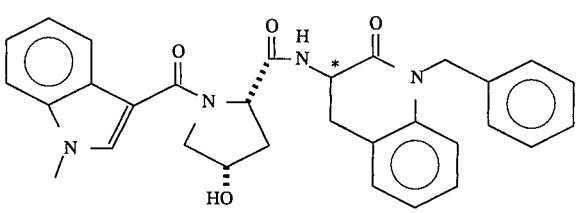
*R/S
Example 205
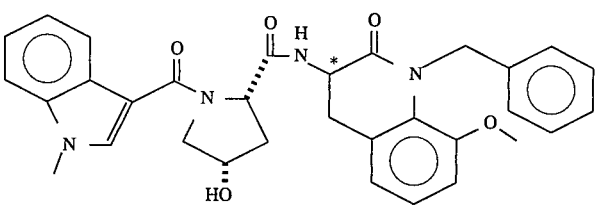
*R/S
Example 206
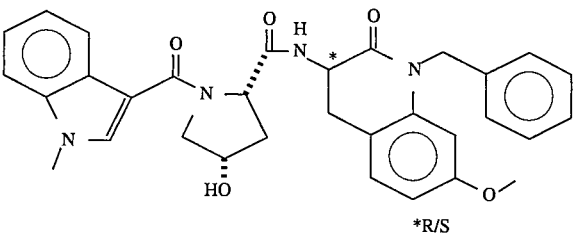
*R/S TABLE 7-continued
Summary of the Examples which may be prepared analogously.
Example 207
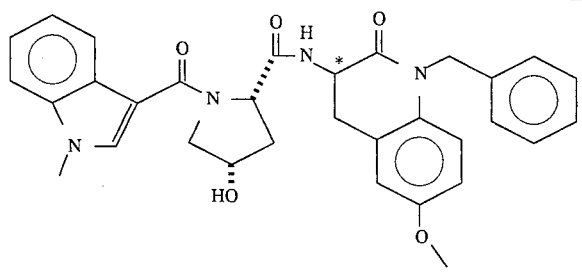
*R/S
Example 208
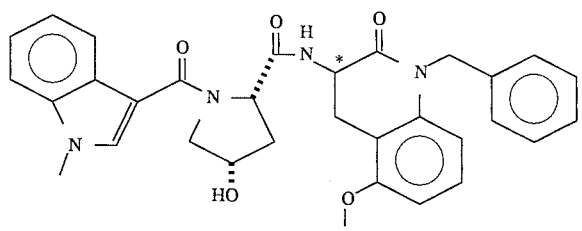
*R/S
Example 209
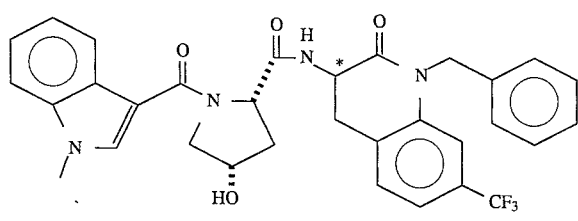
*R/S
Example 210
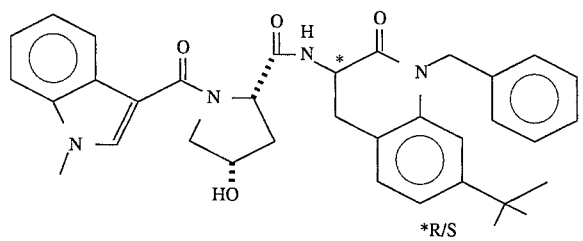
*R/S
Example 211
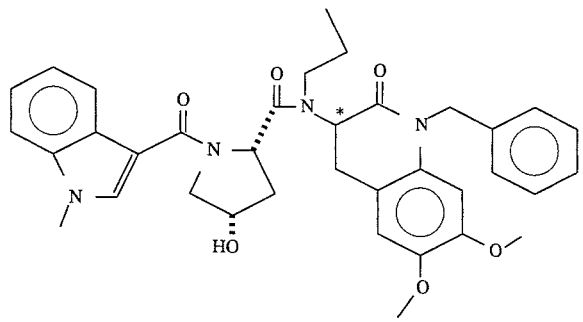
*R/S TABLE 7-continued
Summary of the Examples which may be prepared analogously.
Example 212
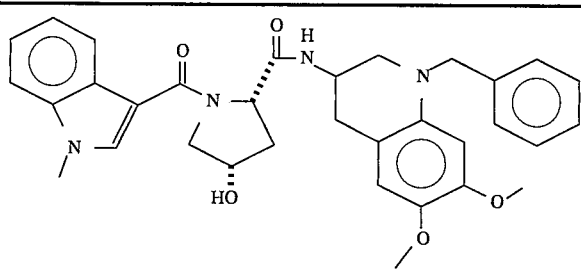
*R/S
Example 213
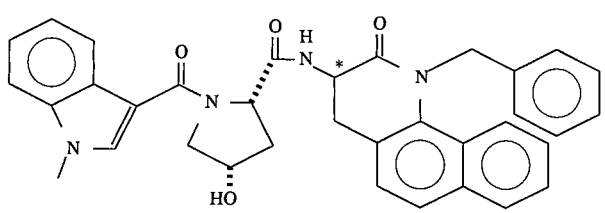
*R/S
Example 214
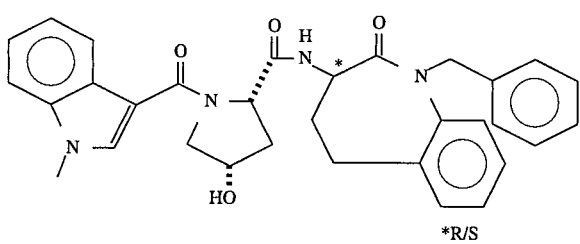
*R/S
Example 215
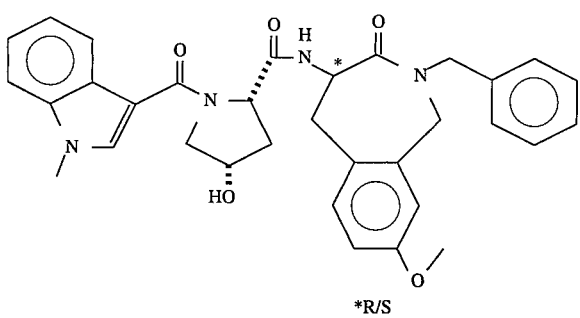
*R/S
Example 216
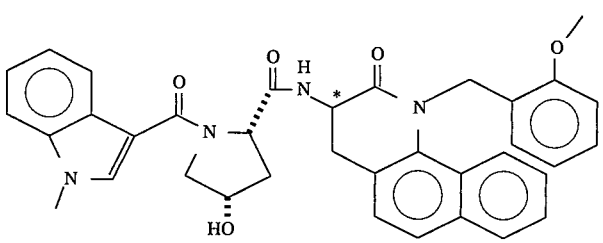
*R/S TABLE 7-continued
Summary of the Examples which may be prepared analogously.
Example 217
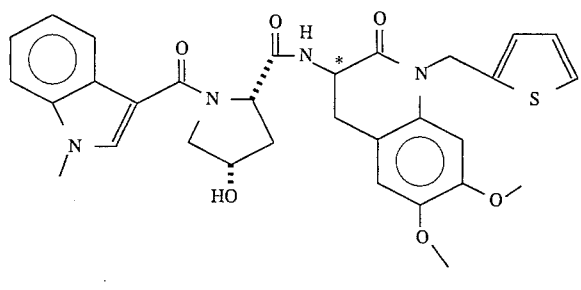
*R/S
Example 218
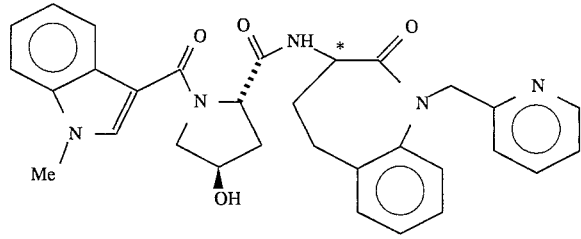
*R/S
Example 219
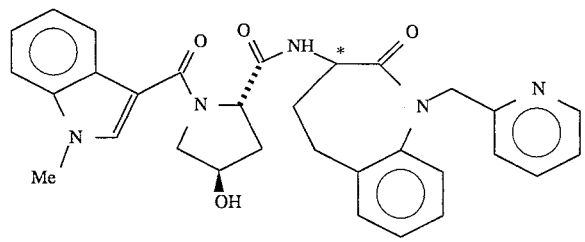
*R/S
Example 220
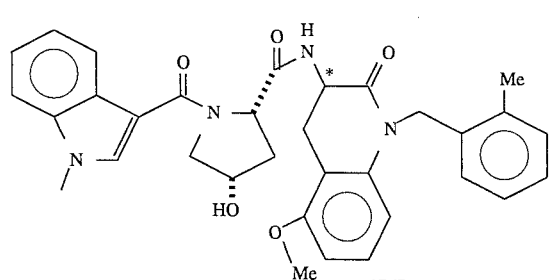
*R/S
Example 221
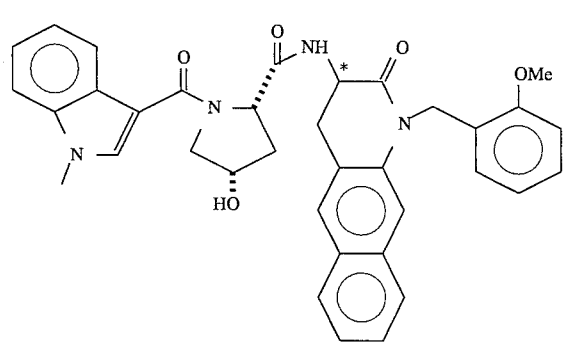
*R/S

Physical Data

The melting points were measured on a Büchi-510-melting point-apparatus, the rotational values on a Perkin-Elmer-241-Polarimeter.

Example 201

M.p.: 128°–142° C. (decomp.); $[\alpha]_D^{20}$ (MeOH)=–103.7° C.

Example 202

M.p.: 201°–208° C.; $[\alpha]_D^{20}$ (DMSO)=–135° C.

Example 203

M.p.: 123°–133° C.; $[\alpha]_D^{20}$ (MeOH)=–24.2° C.

Example 204

M.p.: from 128° C. (decomp.); $[\alpha]_D^{20}$ (MeOH)=–74.2° C.

Example 205

M.p.: from 105° C. (decomp.); $[\alpha]_D^{20}$ (MeOH)=–93.3° C.

Example 206

M.p.: 160°–165° C.; $[\alpha]_D^{20}$ (MeOH)=–135° C.

Example 209

M.p.: 220°–250° C.; $[\alpha]_D^{20}$ (MeOH)=–77.2° C.

Example 210

M.p.: 220°–235° C.; $[\alpha]_D^{20}$ (MeOH)=–101.2° C.

Example 214

M.p.: 118°–123° C.; $[\alpha]_D^{20}$ (MeOH)=–94.2° C.

Example 218

M.p.: 137°–142° C.; $[\alpha]_D^{20}$ (MeOH)=–95.6° C.

Example 219

M.p.: 120°–126° C.; $[\alpha]_D^{20}$ (MeOH)=+27° C.

Example 220

M.p.: 96°–103° C.; $[\alpha]_D^{20}$ (MeOH)=–92.8° C.

Example 221

M.p.: 230°–242° C.; $[\alpha]_D^{20}$ (DMSO)=–65.8° C.

TABLE 8

Examples 222–231

Example 222
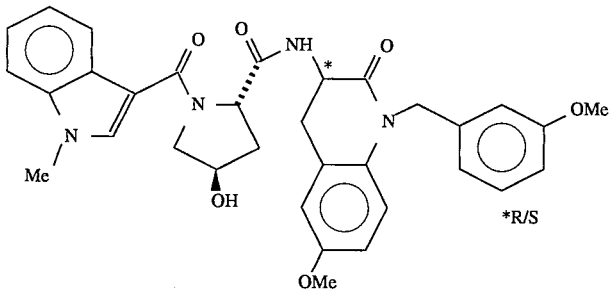
Mp.: 98–104° C.
$[\alpha]_D^{20}$ (MeOH) = –84.2°

Example 223
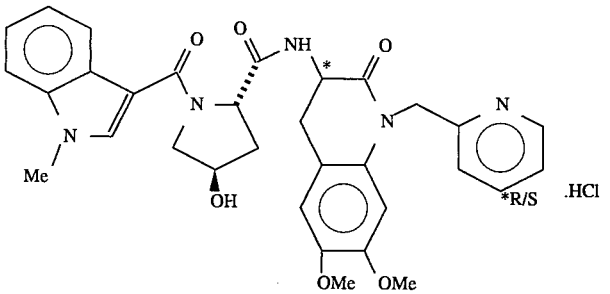
Mp.: 191° C. (dec.)
$[\alpha]_D^{20}$ (MeOH) = –76.4°

Example 224
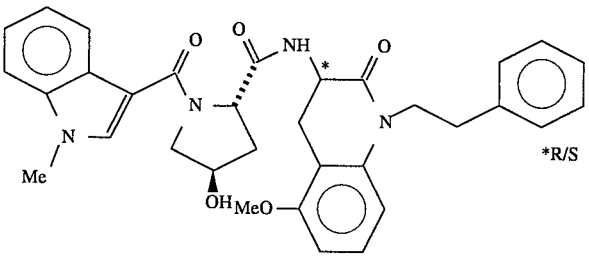
Mp.: 123–128° C.
$[\alpha]_D^{20}$ (MeOH) = –93.2°

TABLE 8-continued
Examples 222–231
Example 225 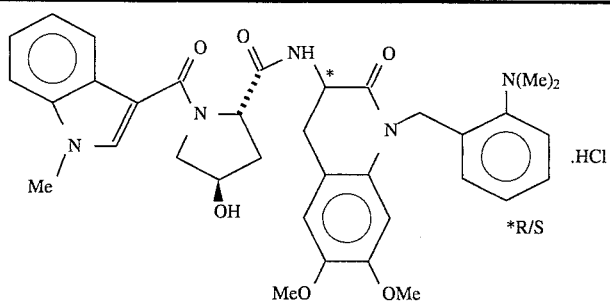
Mp.: 182° C. (dec.)
$[\alpha]_D^{20}$ (MeOH) = −77.8°
Example 226 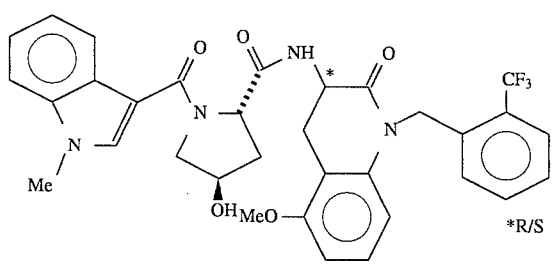
Mp.: 147–154° C.
$[\alpha]_D^2$ (MeOH) = −80.2°
Example 227 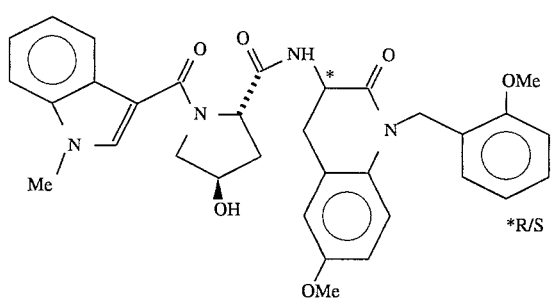
Mp.: 136–148° C.
$[\alpha]_D^{20}$ (MeOH) = −86.0°
Example 228 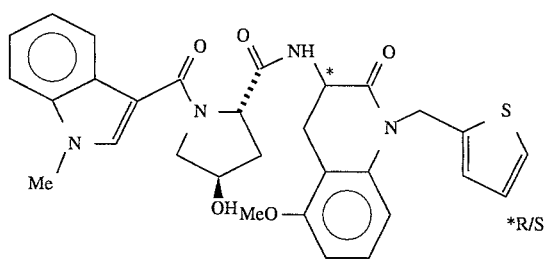
Mp.: 131–141° C.
$[\alpha]_D^{20}$ (MeOH) = −99.6°
Example 229 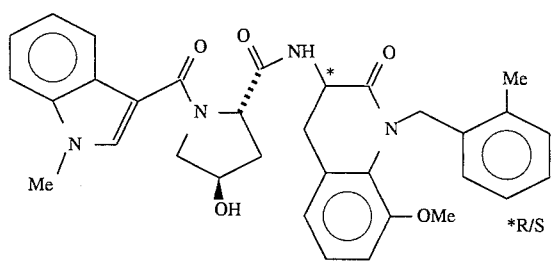
Mp.: 141–143° C.
$[\alpha]_D^{20}$ (MeOH) = −106.6°

TABLE 8-continued

Examples 222–231

Example 230 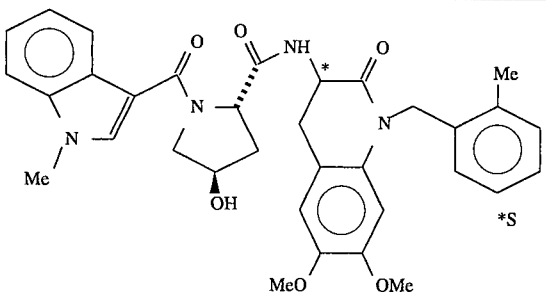

Mp.: 178–180° C.
$[\alpha]_D^{20}$ (MeOH) = –164.8°

Example 231 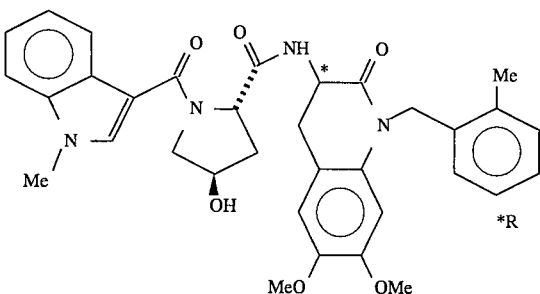

Mp.: 110–120° C. (dec.)
$[\alpha]_D^{20}$ (MeOH) = –19.4°

What is claimed is:

1. A pharmaceutical composition of matter comprising a neurokinin (tachykinin) antagonizing amount of a compound of formula I

wherein

R[1] is vinyl, aryl, heteroaryl, aralkyl, heteroaralkyl, arylvinyl, heteroarylvinyl, aryloxyalkyl, arylalkyloxy, (C$_{3-8}$)cycloalkyl, (C$_{3-8}$)cycloalkylalkyl, bicycloheptyl or bicycloheptylalkyl (either unsubstituted or substituted by 1–3 methyl groups),1 adamantyl, adamantylalkyl, dekaline, dekalinalkyl, tetraline, tetralinalkyl, diphenylalkyl, di(arylalkyl)aminoalkyl or arylalkylaminoalkyl (wherein aryl is phenyl, mono-, di- or trisubstituted phenyl or naphthyl; the substituents of the phenyl group are, independently of each other, halogen, trihalomethyl, alkoxy, alkyl, hydroxy, nitro, alkylcarbonyl or cyano; heteroaryl is indolyl, indolyl substituted in position 1 by alkyl or benzyl, pyridyl, pyrrolyl, imidazolyl or thienyl; and the alkyl and alkoxy group contain 1 to 3 carbon atoms);

A[1] is D- or L-alanine (Ala), (D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ(3,4)-Pro), D- or L-hydroxyproline (Pro(OH)) such as 3-hydroxyproline (Pro(3OH)) and 4-hydroxyproline (Pro(4OH), D- or L-azetidin-2-carboxylic acid (Azt), D- or L-thioproline (Tpr), D- or L-aminoproline (Pro(NH$_2$)) such as 3-aminoproline (Pro(3NH$_2$)) and 4-aminoproline (Pro(4NH$_2$)), D- or L-pyroglutamic acid (pGlu), D- or L-2-aminoisobutyric acid (Aib), D- or L-2,3-diamino-propionic acid, D- or L-2,4-diaminobutyric acid, D- or L-glutamic acid (Glu), D- or L-aspartic acid (Asp), D- or L-glutamine (Gln), D- or L-asparagine (Ash), D- or L-lysine (Lys), D- or L-arginine (Arg), D- or L-histidine (His), D- or L-ornithine Orn), D-or L-hydroxy piperdine carbocylic acid such as 5-hydroxypiperidine-2-carboxylic acid, D- or L-mercaptoproline (Pro(SH)) such as 3-mercaptoproline (Pro(3SH)) and 4-mercaptoproline (Pro(4SH)), Tpr(O), Met(O), Tpr(O$_2$) or Met(O$_2$), and the geometric isomers thereof, whereby the hydroxy and amino groups containing therein may be protected;

B is the group

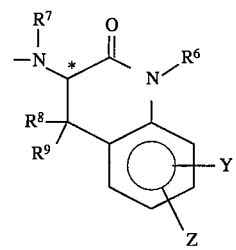

wherein

R[6] is aralkyl, diarylalkyl (in these groups aryl is phenyl or naphthyl and alkyl is (C$_{1-5}$)alkyl), heteroaryl-(C$_{1-5}$)alkyl (wherein heteroaryl is 2-, 3- or 4-pyridyl or 2- or 3-thienyl), phenylamino-(C$_{1-5}$)alkyl, naphthylamino-(C$_{1-5}$)alkyl or N-phenylalkylpiperidinyl (wherein the phenyl groups listed are not substituted or contain 1, 2 or 3 substituents which are, independent of each other, (C$_{1-5}$)alkyl, (C$_{1-5}$)alkoxy, dimethylamine, halogen, trifluoromethyl, —CN or OCF$_3$);

R[7] is hydrogen or (C$_{1-5}$)alkyl; Y and Z independently of each other are hydrogen, (C$_{1-5}$)alkyl; (C$_{1-5}$)alkyloxy, benzyloxy (wherein the phenyl group is not substituted or contains 1,2 or 3 substituents which are independently of each other (C$_{1-5}$)alkyl, (C$_{1-5}$)alkoxy, dimethylamine, halogen, trifluoromethyl, —CN or OCF₃), OCF₃, halogen, CF₃, CN, CH₂NH₂, CONH₂, N-(C₁₋₅-alkyl)₂, NH-(C₁₋₄)alkylcarbonyl, N-(C₁₋₅)alkyl-N-(C₁₋₄)alkylcarbonyl, NH₂ or NH-(C₁₋₅)alkyl or if Y and Z are in a vicinal position to one another, both together represent —OCH₂O—, OCH₂CH₂O— or (CH₂)₄

R⁸ is hydrogen and R⁹ is hydroxy, (C₁₋₅)alkoxy, phenyl-(C₁₋₅)alkyloxy, naphthyl(C₁₋₅)alkyloxy or (C₁₋₄)alkylcarbonyl, or wherein R⁸ and R⁹ are both oxygen or —OCH₂CH₂O—;

and the chirality to C* may be R or S, or the pharmaceutically acceptable salts thereof, and an inert carrier or excipient.

2. The pharmaceutical composition as recited in claim 1, wherein in the compound of formula I R¹ is vinyl, aryl, heteroaryl, aralkyl, heteroaralkyl, arylvinyl, heteroarylvinyl, aryloyalkyl, arylalkyloxy, di(arylalkyl)aminoalkyl or arylalkylaminoalkyl (wherein aryl is phenyl, mono-, di- or trisubstituted phenyl or naphthyl; the substituents of the phenyl group, independently of each other, are halogen, trihalomethyl, alkoxy, alkyl or cyano; heteroaryl is indolyl, indolyl substituted in position 1 by alkyl or benzyl, pyridyl, pyrrolyl, imidazolyl or thienyl; and the alkyl and alkoxy groups contain 1 to 3 carbon atoms); and A¹ is D- or L-alanine (Ala), D- or L-valine (Val), D- or L-leucine (Leu), D- or L-isoleucine (Ile), D- or L-serine (Ser), D- or L-threonine (Thr), D- or L-allothreonine, D- or L-cysteine (Cys), D- or L-methionine (Met), D- or L-phenylalanine (Phe), D- or L-tryptophan (Trp), N-formyl protected Trp, D- or L-tyrosine (Tyr), D- or L-proline (Pro), D- or L-didehydroproline (ΔPro) such as 3,4-didehydroproline (Δ(3,4)-Pro), D- or L-hydroxyproline (Pro(OH)) such as 3-hydroxyproline (Pro(3OH)) and 4-hydroxyproline (Pro(4OH), D- or L-azetidin-2-carboxylic acid (Azt), D- or L-thioproline (Tpr), D- or L-aminoproline (Pro(NH₂)) such as 3-aminoproline (Pro(3NH₂)) and 4-aminoproline (Pro(4NH₂)), D- or L-pyroglutamic acid (pGlu), D- or L-2-aminoisobutyric acid (Aib), D- or L-2,3-diaminopropionic acid, D- or L-2,4-diaminobutyric acid, D- or L-glutamic acid (Glu), D- or L-aspartic acid (Asp), D- or L-glutamine (Gln), D- or L-asparagine (Asn), D- or L-lysine (Lys), D- or L-arginine (Arg), D- or L-histidine (His), D- or L-ornithine (Orn), D-or L-hydroxy piperdine carbocylic acid such as 5-hydroxypiperidine-2-carboxylic acid, D- or L-mercaptoproline (Pro(SH)) such as 3-mercaptoproline (Pro(3SH)) and 4-mercaptoproline (Pro(4SH)), Tpr(O), Met(O), Tpr(O₂) or Met(O₂), and the geometric isomers thereof, whereby the hydroxy and amino groups contained therein may be protected.

3. The pharmaceutical composition as recited in claim 1 wherein in the compound of formula I the hydroxy and amino groups contained in A¹ are protected by acyl, carbamoyl or aralkyl.

4. The pharmaceutical composition as recited in claim 3 wherein the hydroxy and amino groups contained in A¹ are protected by benzyl.

5. The pharmaceutical composition as recited in claim 1 wherein in the compound of formula I R¹ is aryl, heteroaryl, aralkyl, heteroaralkyl, aryloxyalkyl, arylalkyloxy, di(arylalkyl)aminoalkyl (wherein aryl denotes phenyl or mono- or disubstituted phenyl; the substituents of the phenyl group independently of each other are halogen or alkoxy; heteroaryl denotes indolyl, indolyl substituted by alkyl or benzyl in position 1; and the alkyl or alkoxy group contains 1 to 3 carbon atoms.

6. The pharmaceutical composition as recited in claim 5 wherein R¹ is

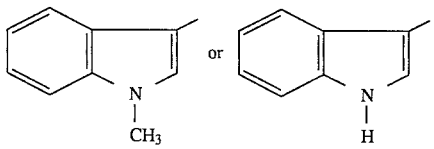

7. The pharmaceutical composition as recited in claim 6 wherein R¹ is

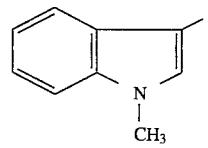

8. The pharmaceutical composition as recited in claim 1 wherein in the compound of formula I, A¹ is an amino acid which carries one or 2 polar functional group(s) in the side chain such as OH, COOH, NH₂, guanidine, CONH₂, or SH.

9. The pharmaceutical composition as recited in claim 8, wherein the functional group in the side chain of A¹ is OH.

10. The pharmaceutical composition as recited in claim 1 wherein in the compound of formula I, A¹ is Ser, Thr, Trp(For) or Tyr.

11. The pharmaceutical composition as recited in claim 1, wherein in the compound of formula I, A¹ is Pro or 4-hydroxyproline.

12. The pharmaceutical composition as recited in claim 11 wherein A¹ is 4-hydroxyproline with 2-S-configuration.

13. The pharmaceutical composition as recited in claim 1, wherein in the compound of formula I, R⁶ is benzyl or methoxybenzyl.

14. The pharmaceutical composition as recited in claim 1, wherein in the compound of formula I, R⁷ is hydrogen.

15. The pharmaceutical composition as recited in claim 1, wherein in the compound of formula I, Y and Z, independently of each other, are methoxy, hydrogen, CF₃ or tert.butyl or together —(CH)₄—.

16. The pharmaceutical composition as recited in claim 1, wherein the compound of formula I is selected from the group consisting of:

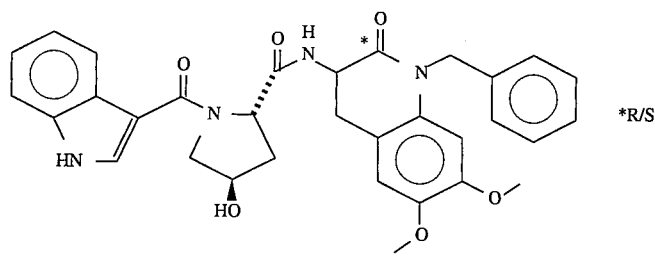 *R/S
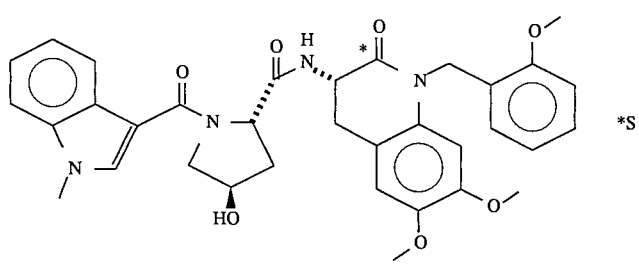 *S
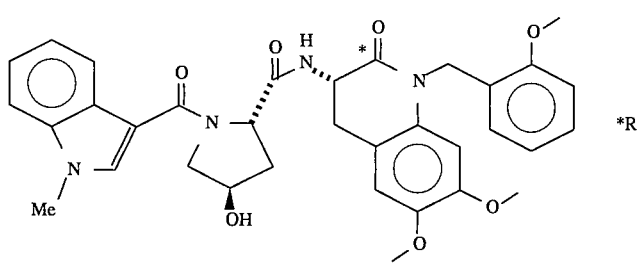 *R
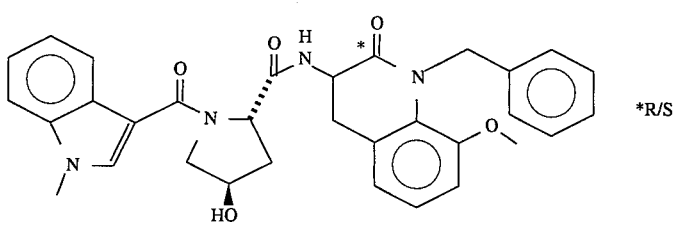 *R/S
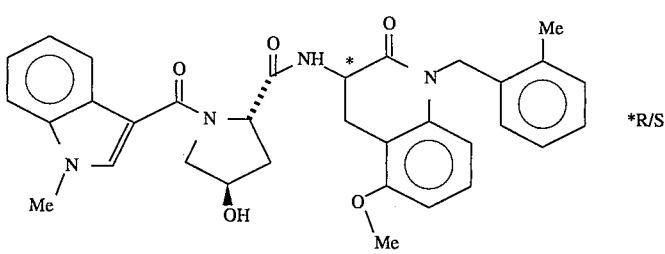 *R/S
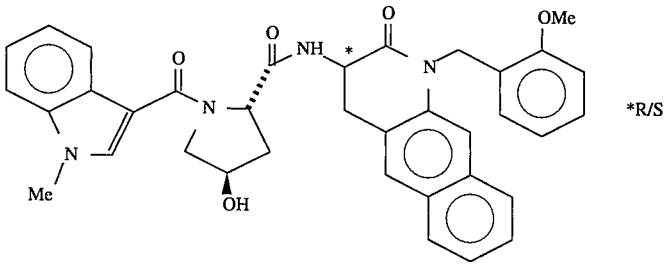 *R/S -continued
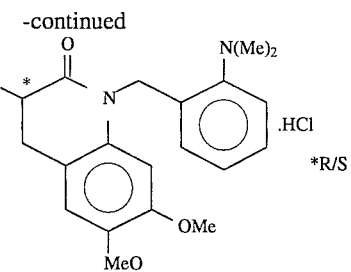
*R/S
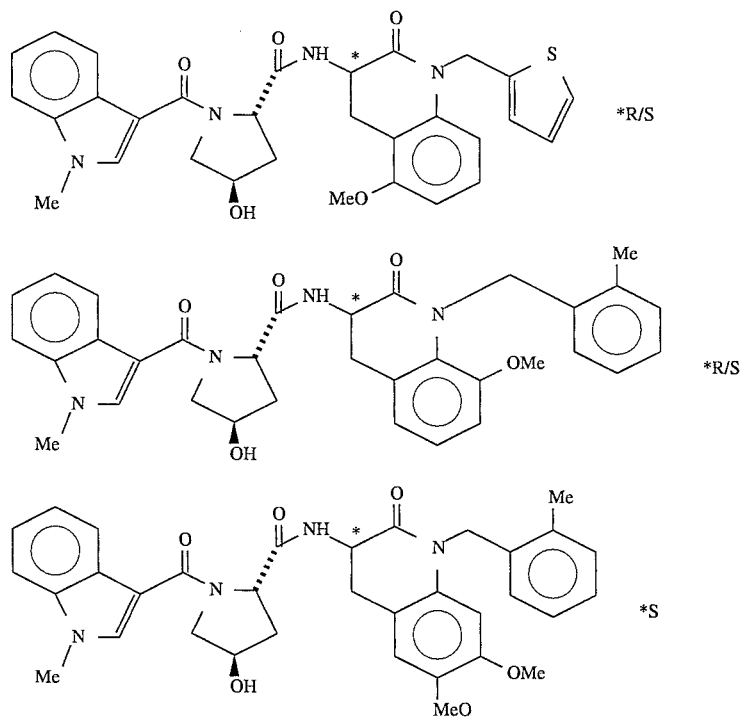
*R/S
*R/S
*S
and
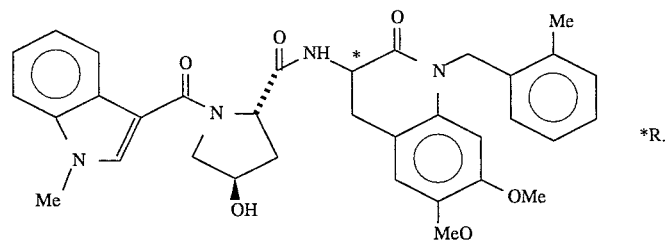
*R.
* * * * *